United States Patent
Lodish et al.

(10) Patent No.: US 11,371,019 B2
(45) Date of Patent: Jun. 28, 2022

(54) EFFICIENT GENERATION OF HUMAN RED BLOOD CELLS VIA ENRICHING PERIPHERAL BLOOD ERYTHROID PROGENITORS

(71) Applicant: Whitehead Institute for Biomedical Research, Cambridge, MA (US)

(72) Inventors: Harvey Lodish, Brookline, MA (US); Xiaofei Gao, Cambridge, MA (US); Hsiang-Ying Lee, Cambridge, MA (US)

(73) Assignee: Whitehead Institute for Biomedical Research, Cambridge, MA (US)

( * ) Notice: Subject to any disclaimer, the term of this patent is extended or adjusted under 35 U.S.C. 154(b) by 385 days.

(21) Appl. No.: 16/081,718

(22) PCT Filed: Mar. 3, 2017

(86) PCT No.: PCT/US2017/020702
§ 371 (c)(1),
(2) Date: Aug. 31, 2018

(87) PCT Pub. No.: WO2017/152077
PCT Pub. Date: Sep. 8, 2017

(65) Prior Publication Data
US 2019/0093080 A1 Mar. 28, 2019

Related U.S. Application Data

(60) Provisional application No. 62/303,988, filed on Mar. 4, 2016.

(51) Int. Cl.
| | | |
|---|---|---|
| *C12N 5/078* | (2010.01) | |
| *A61K 31/573* | (2006.01) | |
| *A61K 35/18* | (2015.01) | |
| *G01N 33/50* | (2006.01) | |

(52) U.S. Cl.
CPC .......... *C12N 5/0641* (2013.01); *A61K 31/573* (2013.01); *A61K 35/18* (2013.01); *G01N 33/502* (2013.01); *G01N 33/5014* (2013.01); *G01N 33/5044* (2013.01); *C12N 2501/125* (2013.01); *C12N 2501/14* (2013.01); *C12N 2501/2303* (2013.01); *C12N 2501/33* (2013.01); *C12N 2501/998* (2013.01); *C12N 2501/999* (2013.01)

(58) Field of Classification Search
None
See application file for complete search history.

(56) References Cited

U.S. PATENT DOCUMENTS 6,361,998 B1 * 3/2002 Bell ............ C12N 5/0641
 435/407
2012/0295285 A1 * 11/2012 An ............ G01N 33/56966
 435/7.25

FOREIGN PATENT DOCUMENTS

| WO | WO 2007/038664 A1 | 4/2007 | |
|---|---|---|---|
| WO | WO-2007038664 A1 * | 4/2007 | ......... G01N 33/5014 |
| WO | WO 2011/113036 A2 | 9/2011 | |
| WO | WO 2013/078286 A1 | 5/2013 | |

OTHER PUBLICATIONS

International Search Report and Written Opinion, dated Jul. 17, 2017, in connection with PCT/US2017/020702.
International Preliminary Report on Patentability, dated Sep. 13, 2018, in connection with PCT/US2017/020702.
Invitation to Pay Additional Fees, mailed May 11, 2017, in connection with PCT/US2017/020702.
Akhurst et al., Targeting the TGFβ signalling pathway in disease. Nat Rev Drug Discov. Oct. 2012;11(10):790-811. doi: 10.1038/nrd3810. Epub Sep. 24, 2012.
Fortunel et al., Transforming growth factor-beta: pleiotropic role in the regulation of hematopoiesis. Blood. Sep. 15, 2000;96(6):2022-36.
Heddle et al., Micronuclei as an index of cytogenetic damage: past, present, and future. Environ Mol Mutagen. 1991;18(4):277-91.
Li et al., Isolation and transcriptome analyses of human erythroid progenitors: BFU-E and CFU-E. Blood. Dec. 4, 2014;124(24):3636-45. doi:10.1182/blood-2014-07-588806. Epub Oct. 22, 2014.
Sawada et al., Human colony-forming units-erythroid do not require accessory cells, but do require direct interaction with insulin-like growth factor I and/or insulin for erythroid development. J Clin Invest. May 1989;83(5):1701-9.

* cited by examiner

*Primary Examiner* — Emily A Cordas
(74) *Attorney, Agent, or Firm* — Wolf, Greenfield & Sacks, P.C.

(57) ABSTRACT

A population of early-stage burst-forming unit-eryhtoid (BFU-E) cells characterized by low expression of the Type III Transforming Growth Factor β Receptor (TGFRPIII) and uses thereof for producing red blood cells in vitro, genotoxicity analysis of chemicals, drug sensitivity assessment, and drug development. Also described herein are methods for producing the population of early-stage BFU-E cells and methods for producing red blood cells.

28 Claims, 11 Drawing Sheets

Differentiation of Human TGFBR3$^{lo}$ CD71$^{hi}$ BFU-E progenitors

EFFICIENT GENERATION OF HUMAN RED BLOOD CELLS VIA ENRICHING PERIPHERAL BLOOD ERYTHROID PROGENITORS

RELATED APPLICATIONS

This application is a national stage filing under 35 U.S.C. § 371 of international PCT application, PCT/US2017/020702, filed Mar. 3, 2017, which claims priority under 35 U.S.C. § 119(e) to U.S. Provisional Patent Application No. 62/303,988, filed Mar. 4, 2016, the entire contents of each of which are incorporated by reference herein.

GOVERNMENT SUPPORT

This invention was made with government support under Grant No. HL032262, awarded by the National Institutes of Health. The government has certain rights in this invention.

BACKGROUND OF THE INVENTION

Burst-forming unit-erythroid (BFU-E) cells are erythroid progenitor cells capable of generating in methylcellulose culture colonies of erythroid cells that contains "bursts" of smaller erythroid colonies derived from the later colony-forming unit-erythroid (CFU-E) cells, which are erythropoietin (Epo)-dependent erythroid progenitors. Early-stage BFU-E cells are presumably having higher capacities for self-renewal than do those BFU-E cells forming small BFU-E colonies. Thus, early-stage BFU-E cells would be a suitable erythroid progenitor cell population for various uses, including therapeutic uses, genotoxicity assays, and drug development.

Traditionally, in vivo micronucleus tests using animals were applied to assess genotoxicity from chemicals. Such tests require injecting a test chemical to animals and then isolate red blood cells (RBCs) from the bone marrow of the animals. An increase in the frequency of micronucleus formation in treated animals is an indication of induced chromosome damage genotoxicity. This traditional in vivo genotoxicity assay is time consuming and usually do not provide useful information of chemicals that are not systemically absorbed.

SUMMARY OF THE INVENTION

The present disclosure is based on the unexpected discovery that the Type III Transforming Growth Factor β Receptor (TGFβRIII) can serve as a biomarker to distinguish early stage burst-forming unit-erythroid (BFU-E) cells from late-stage BFU-E cells. Early-stage BFU-E cells have higher renewal capacity and thus are capable of forming larger colonies as compared with late-stage BFU-E cells.

Accordingly, one aspect of the present disclosure provides a method for producing a population of early-stage burst-forming unit-erythroid (BFU-E) cells capable of forming BFU-E colonies having at least 12 cell clusters as determined by a methylcellulose assay; the method comprising: (i) providing a population of erythroid progenitor cells; and (ii) isolating from the population of (i) cells expressing a low level of Type III Transforming Growth Factor β Receptor (TGFβRIII), thereby producing the population of early-stage BFU-E cells. In some embodiments, the isolating step is performed by isolating from the population of (i) the 1-40% cells expressing the lowest level of TGFβRIII, e.g., the 10-20% cells expressing the lowest level of TGFβRIII.

In some embodiments, the population of erythroid progenitor cells of (i) is derived from human peripheral blood cells. The erythroid progenitor cells may be prepared by isolating mononuclear cells from the human peripheral blood cells and culturing the mononuclear cells in a culture medium for 1 to 6 days. The culture medium may comprise interleukin 3 (IL-3), stem cell factor (SCF), erythropoietin (Epo), and a steroid, which can be dexamethasone (DEX).

In methods described herein that involve the use of human peripheral blood cells, the isolating step can be performed by isolating cells that express a low level of TGFβRIII and a high level of CD71. For example, the isolating step may be performed by harvesting the overlapping population of (a) the 1-40% cells expressing the lowest TGFβRIII, and (b) the 40-50% of cells expressing the highest level of CD71. Alternatively, the isolating step may be performed by harvesting the overlapping population of (a) the 10-20% cells expressing the lowest TGFβRIII, and (b) the 40-50% of cells expressing the highest level of CD71. In one example, the isolating step is performed by harvesting the overlapping population of (a) the 10% cells expressing the lowest TGFβRIII, and (b) the 40% of cells expressing the highest level of CD71.

In other embodiments, the population of erythroid progenitor cells of (i) is derived from human cord blood CD34$^+$ cells. The erythroid progenitor cells can be prepared by culturing the human cord blood CD34+ cells in a first culture medium for 1 to 6 days to enrich erythroid progenitor cells and culturing the enriched erythroid progenitor cells in a second culture medium for 1 to 6 days. The first culture medium may comprise interleukin 3 (IL-3), stem cell factor (SCF), erythropoietin (Epo), and a steroid (e.g., DEX).

In methods described herein that involve the use of human cord blood, the isolating step is performed by isolating cells that express a low level of TGFβRIII and a low level of CD71. For example, the isolating step may be performed by isolating the overlapping population of (a) the 1-40% cells expressing the lowest TGFβRIII, and (b) the 40-50% of cells expressing the lowest level of CD71. In another example, the isolating step may be performed by isolating the overlapping population of (a) the 10-20% cells expressing the lowest TGFβRIII, and (b) the 40-50% of cells expressing the lowest level of CD71. In yet another example, the isolating step is performed by isolating the overlapping population of (a) the 10% cells expressing the lowest TGFβRIII, and (b) the 40% of cells expressing the lowest level of CD71. Alternatively or in addition, the second culture medium comprises human transferrin, SCF, Epo, insulin, IL-3 and a steroid such as DEX.

In another aspect, the present disclosure features a population of isolated early-stage burst-forming unit-erythroid (BFU-E) cells in a culture medium, wherein the early-stage BFU-E cells are characterized by low expression of TGFβRIII In some embodiments, the early-stage BFU-E cells are derived from human peripheral blood and are further characterized by high expression of CD71. In other embodiments, the early-stage BFU-E cells are derived from human cord blood and are further characterized by low expression of CD71. The culture medium may comprise interleukin 3 (IL-3), stem cell factor (SCF), erythropoietin (Epo), and optionally steroid, which can be DEX.

The population of early-stage burst-forming unit-erythroid (BFU-E) cells characterized by low expression of TGFβRIII as described herein can be used for treating a disease associated with abnormal blood cells, e.g., any of those described herein. A disease associated with abnormal blood cells may have abnormal blood cells and/or the number of blood cells may be abnormally low due, e.g., to abnormally low production or abnormally increased destruction. In some embodiments, such a treatment comprises administering a subject in need thereof the population of early-stage BFU-E cells, which may be autologous or allogeneic. In some examples, the early-stage BFU-E cells are derived from human peripheral blood and are further characterized by high expression of CD71. In other examples, the population of early-stage BFU-E cells is derived from human cord blood and is further characterized by low expression of CD71. In some embodiments, such a treatment comprises administering to a subject in need thereof, cells derived ex vivo from the population of early-stage BFU-E cells, which may be autologous or allogeneic. For example, the treatment may comprise administering erythrocytes derived ex vivo from the population of early-stage BFU-E cells.

Also described herein is a method for assessing genotoxicity effect of an agent; comprising: (i) providing a population of early-stage burst-forming unit-erythroid (BFU-E) cells, which is characterized by low expression of TGFβRIII; (ii) culturing the early-stage BFU-E cells in a first culture medium for 1 to 8 days to expand the BFU-E population; (iii) culturing the expanded BFU-E cells in a second culture medium in the presence of an agent for 4 to 12 days under conditions allowing for differentiation of the BFU-E cells; (iv) harvesting the differentiated erythroid cells; (v) determining DNA damage level of the differentiated erythroid cells; and (vi) evaluating genotoxicity effect of the agent based on the DNA damage level determined in (v); wherein a higher DNA damage level of the differentiated erythroid cells relative to that of differentiated erythroid cells produced in the absence of the agent indicates genotoxicity effect of the agent. The DNA damage level can be determined by measuring (i) the frequency of micronuclei (MN) of the differentiated erythroid cells, or (ii) number, size, shape, or a combination thereof, of the polychromatic erythrocytes in the differentiated erythroid cells.

The genotoxicity assay can be used to assess the genotoxicity of agents on a personalized level. For instance, the assay may be used to test agents to which the particular human subject from whom the BFU-E cells were derived may be exposed. For example, agents to which the subject may be exposed in his or her work environment may be tested.

An agent tested in the assay may be a small molecule. For instance, small molecules e.g., agents used or contemplated for use in industrial processes (e.g., manufacturing), agents used or contemplated for use in products of any kind such as food products, personal care products, cosmetics, cooking products, agents used or contemplated for use in agriculture or gardening (e.g., pesticides, herbicides), etc could be tested. Waste materials resulting from industrial processes could be tested. Multiple different concentrations of a test agent could be tested, e.g., to determine a level that results in no detectable genotoxicity.

In some examples, the early-stage BFU-E cells are derived from human peripheral blood and are further characterized by high expression of CD71. In other examples, the early-stage BFU-E cells are derived from human cord blood and are further characterized by low expression of CD71.

In any of the methods described above, the first culture medium may comprise interleukin 3 (IL-3), stem cell factor (SCF), erythropoietin (Epo), and a steroid such as dexamethasone (DEX). When the early-stage BFU-E cells are derived from human cord blood, the first medium may further comprise human transferrin and insulin. Alternatively or in addition, second culture medium comprises human transferrin, insulin, SCF, and Epo.

In some examples, the early-stage BFU-E cells are derived from a healthy human subject. In other examples, the early-stage BFU-E cells are derived from a human patient who has a disease. In that case, the agent may be a therapeutic agent, and wherein the genotoxicity effect of the agent as determined in (vi) indicates that the human patient is sensitive to the therapeutic agent.

Further, the present disclosure provides a method for screening for a drug candidate for treating a disease associated with abnormal blood cells and/or an abnormally low number of blood cells, the method comprising: (i) providing a population of early-stage burst-forming unit-erythroid (BFU-E) cells, which is characterized by low expression of TGFβRIII; (ii) culturing the BFU-E cells of (i) in a culture medium in the presence of an agent for 4 to 12 days under conditions allowing for differentiation of the BFU-E cells; (iii) measuring the total number of erythroid cells in the cell culture; wherein an increase of the total erythroid cells as compared to that of a same early-stage BFU-E cell culture cultured in the absence of the agent indicates that the agent is a drug candidate for treating the disease. Diseases associated with abnormal blood cells and/or abnormally low number of blood cells or as otherwise described herein include anemia (e.g., Diamond Blackfan anemia or DBA. Other causes of anemia may be associated with decreased RBC production, increased RBC destruction, blood loss (e.g., due to trauma, gastrointestinal bleeding), etc. In some embodiments the anemia is an Epo-resistant anemia), thalessemias (a cause of anemia), polycythemia vera, erythroid leukemia, and myelodysplastic syndrome (MDS). The assays are also useful for screening for agents that reduces the total number of erythroid cells. When the assay is used to screen for agents for the treatment of thalassemia, the identified agent may be one that increases the amount of fetal hemoglobin. In some examples, the early-stage BFU-E cells are derived from human peripheral blood and are further characterized by high expression of CD71. In other examples, the early-stage BFU-E cells are derived from human cord blood and are further characterized by low expression of CD71.

The culture medium may comprise human transferrin, SCF, Epo, and optionally insulin. Alternatively, the culture medium may further comprise IL-3 and a steroid such as DEX.

Moreover, the present disclosure features a method for assessing genotoxicity effect of an agent; comprising: (i) providing a population of human peripheral mononuclear blood cells (PBMC) that contain erythroid progenitor cells; (ii) culturing the population of PBMCs in a first culture medium for 4 to 12 days to expand the erythroid progenitor cells in the PBMCs; (iii) culturing the expanded cells in a second culture medium in the presence of an agent for 4 to 12 days under conditions allowing for differentiation of the erythroid progenitor cells; (iv) harvesting the differentiated erythroid cells; (v) determining DNA damage level of the differentiated erythroid cells; and (vi) evaluating genotoxicity effect of the agent based on the DNA damage level determined in (v); wherein a higher DNA damage level of the differentiated erythroid cells relative to that of differentiated erythroid cells produced in the absence of the agent indicates genotoxicity effect of the agent. The first culture medium comprises interleukin 3 (IL-3), stem cell factor (SCF), erythropoietin (Epo), and a steroid, such as DEX.

Alternatively or in addition, the second culture medium may comprise human transferrin, SCF, Epo, and optionally insulin.

In some embodiments, the DNA damage level is determined by measuring (i) the frequency of micronuclei (MN) of the differentiated erythroid cells, or (ii) number, size, shape, or a combination thereof, of the polychromatic erythrocytes in the differentiated erythroid cells.

The PBMCs may be derived from a healthy human subject who has a high level of erythroid progenitor cells in the PBMCs. Alternatively, the PBMCs may be derived from a human patient who has a disease and a high level of erythroid progenitor cells in the PBMCs. In that case, the agent can be a therapeutic agent, and wherein the genotoxicity effect of the agent as determined in (vi) indicates that the human patient is sensitive to the therapeutic agent.

Also within the scope of the present disclosure is a method for producing red blood cells (RBCs), the method comprising: (i) providing a first population of erythroid progenitor cells; (ii) isolating from the first population of erythroid progenitor cells an early stage burst-forming unit-erythroid (BFU-E) subpopulation, which is characterized by low expression of Type III Transforming Growth Factor β Receptor (TGFβRIII); (iii) expanding the BFU-E subpopulation of (ii) in a first culture medium for, e.g., 1 to 8 days, to produce a second population of erythroid progenitor cells; and (iv) differentiating the second population of erythroid progenitor cells in a second culturing medium for, e.g., 1 to 8 days, to produce red blood cells (RBCs).

In some embodiments, the first culture medium comprises interleukin 3 (IL-3), stem cell factor (SCF), erythropoietin (Epo), and a steroid such as DEX. Alternatively or in addition, the second culture medium can be an erythroid differentiation medium, which comprises human transferrin, SCF, Epo, and optionally insulin.

In some embodiments, the first population of erythroid progenitor cells is derived from human peripheral blood cells. The early-stage BFU-E subpopulation may be composed of TGFβRIII$^{lo}$/CD71$^{hi}$ erythroid progenitor cells. In some examples, the first population of erythroid progenitor cells can be prepared by isolating mononuclear cells from the human peripheral blood cells and culturing the mononuclear cells in the first culture medium for 1-8 days.

In other embodiments, the first population of erythroid progenitor cells is derived from human cord blood CD34$^+$ cells. The early-stage BFU-E subpopulation is composed of TGFβRIII$^{lo}$/CD71$^{hi}$ erythroid progenitor cells. In some examples, the first population of erythroid progenitor cells is prepared by culturing the human cord blood CD34$^+$ cells in the first culture medium for 1 to 6 days to enrich erythroid progenitor cells and culturing the enriched erythroid progenitor cells in a third culture medium for 1 to 6 days. The third culture medium comprises human transferrin, IL-3, SCF, insulin, a steroid (e.g., DEX) and Epo. In some instances, the first culture medium can be identical to the third culture medium.

Further, the present disclosure provides a method for treating a disease associated with abnormal blood cells (e.g., those described herein), comprising administering to a subject in need thereof an effective amount of an agent that blocks the TGF-β signaling pathway or expands BFU-E in vitro. In some embodiments, the subject is a human patient having or suspected of having Diamond Blackfan Anemia (DBA). In some examples, the agent is a TGFβ receptor I kinase inhibitor, for example, galunisertib.

Also within the scope of the present disclosure are the early-stage BFU-E cells or the TGFβ inhibitor for use in treating a disease associated with abnormal blood cells (such as those described herein) and uses of the early-stage BFU-E cells or the TGFβ inhibitor for manufacturing a medicament for use in treating the disease.

The details of one or more embodiments of the invention are set forth in the description below. Other features or advantages of the present invention will be apparent from the following drawings and detailed description of several embodiments, and also from the appended claims.

DETAILED DESCRIPTION OF THE INVENTION

Figure 1:
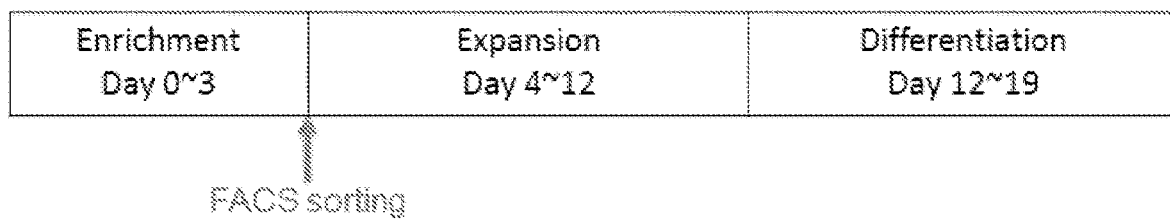
FIG. 1. A diagram showing an exemplary human erythroid progenitor enrichment and culture platform. Top panel: Culture scheme using human peripheral blood. Bottom panel: Culture scheme using human cord blood CD34$^+$ cells.
Figure 1:
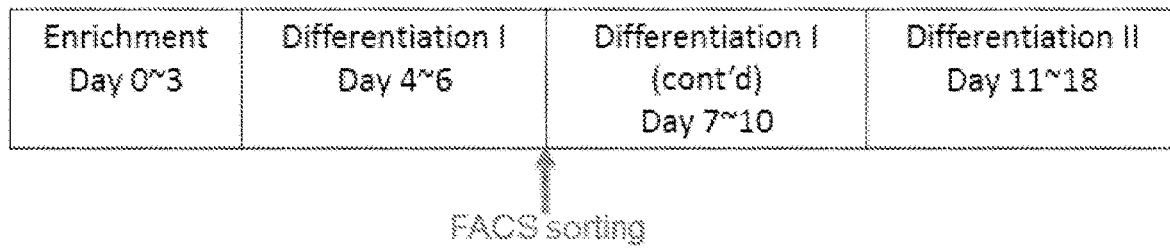

Described herein are early-stage BFU-E cells characterized by low expression of TGFβRIII, methods for preparing such a erythroid progenitor cell population, uses of this erythroid progenitor cell population for treating diseases associated with abnormal blood cells, for producing red blood cells (RBCs), for genotoxicity analysis, for drug sensitivity assessment, and for drug development. Also described herein are methods of treating diseases associated with abnormal blood cells using an agent that inhibits the TGFβ signaling pathway.

I. Early-Stage BFU-E Cells and Methods for Preparing Such (i) Early-stage BFU-E cells The early-stage BFU-E cells described herein are a subpopulation of BFU-E cells characterized by low expression of TGFβRIII This erythroid progenitor cell population is composed of the 1-40% (e.g., 5-35%, 10-30%, 10-20%, or 10%) of the total BFU-E cells expressing the lowest amount of surface TGFβRIII The early-stage BFU-E cells have higher renewal capacity as compared with late-stage BFU-E cells, which express a high level of TGFβRIII As such, the early-stage BFU-E cells can form large colonies. The colony formation ability of BFU-E cells can be determined by conventional methods, for example, the methylcellulose assay. Sawada et al., J. Clin. Invest. (1989) 83(5):1701-1709. In some examples, the early-stage BFU-E cells can form colonies each containing at least 12 cell clusters as determined by the methylcellulose assay.

A progenitor cell, like a stem cell, has a tendency to differentiate into a specific type of cell. Progenitor cells are usually more specific than stem cells and are often pushed to differentiate into the target cells.

As used herein, erythroid progenitor cells refer to any cell that can be induced to undergo erythropoiesis in vivo or in vitro. These erythroid progenitors will most preferably be near the CFU-E stage of erythropoiesis, but they may also be at an earlier stage of erythroid development, such as the burst-forming unit erythroid (BFU-E) stage of development, or at an even earlier stage of hematopoietic development such as the CFU-granulocyte erythroid macrophage megakaryocyte (CFU-GEMM or CFU-mix) developmental level.

When the early-stage BFU-E cells are derived from human peripheral blood, such cells may be further characterized by high expression of CD71, which refers to the cell population of the 20-50% (e.g., 30-50% or 40-50%) BFU-E cells that express the highest level of CD71 in the total BFU-E population. In some embodiments, the early-stage BFU-E cells described here are the overlapping population of the 1-40% (e.g., 5-35%, 10-30%, 10-20%, or 10%) BFU-E cells expressing the lowest TGFβRIII and the 20-50% (e.g., 30-50% or 40-50%) BFU-E cells expressing the highest CD71 (TGFβRIII$^{lo}$/CD71$^{hi}$). For example, the early stage BFU-E cells described herein can be the overlapping population of the 10-20% cells expressing the lowest TGFβRIII and the 40-50% cells that express the highest CD71. In one example, the early-stage BFU-E cells are the overlapping population of the 10% cells expressing the lowest surface TGFβRIII and the 40% cells expressing the highest CD71.

When the early-stage BFU-E cells are derived from human cord blood, such cells may be further characterized by low expression of CD71, which refers to the cell population of the 20-50% (e.g., 30-50% or 40-50%) BFU-E cells that express the lowest level of CD71 in the total BFU-E population. In some embodiments, the early-stage BFU-E cells described here are the overlapping population of the 1-40% (e.g., 5-35%, 10-30%, 10-20%, or 10%) BFU-E cells expressing the lowest TGFβRIII and the 20-50% (e.g., 30-50% or 40-50%) BFU-E cells expressing the lowest CD71)(TGFβRIII$^{lo}$/CD71$^{hi}$). For example, the early stage BFU-E cells described herein can be the overlapping population of the 10-20% cells expressing the lowest TGFβRIII and the 40-50% cells that express the lowest CD71. In one example, the early-stage BFU-E cells are the overlapping population of the 10% cells expressing the lowest surface TGFβRIII and the 40% cells expressing the lowest CD71.

The early-stage BFU-E cell population may be an isolated or purified population of erythroid progenitor cells. Such a population is substantially free of cells and materials with which it is associated in nature, in particular, free of cells that lack the desired phenotype, e.g., expressing a low level of TGFβRIII Substantially free or substantially purified includes at least 50% the early-stage BFU-E cells described herein, preferably at least 70%, more preferably at least 80%, and even more preferably at least 90% the early-stage BFU-E cells described herein.

(ii) Preparation of Early-Stage BFU-E Cell Population

Any of the early-stage BFU cell populations can be prepared by isolating from erythroid progenitor cells BFU-E cells having the features described above via a conventional method. In some examples, the early-stage BFU-E cell population can be isolated by cell sorting, for example, Fluorescence-activated cell sorting (FACS). Techniques providing accurate separation of the early-stage BFU-E cells further include flow cytometry, which can have varying degrees of sophistication, e.g., a plurality of color channels, low angle and obtuse light scattering detecting channels, impedance channels. The early-stage BFU-E cells may also be selected by flow cytometry based on light scatter characteristics, where the target cells are selected based on low side scatter and low to medium forward scatter profiles.

A method for producing the early-stage BFU-E population as described herein may comprise at least the following steps: (i) providing a population of erythroid progenitor cells, and (ii) isolating from the erythroid progenitor cells the early-stage BFU-E cells, which are characterized by low expression of TGFβRIII.

In some embodiments, the erythroid progenitor cells can be derived from human peripheral blood, which can be collected from a suitable subject (e.g., a healthy donor or a human patient having a disease such as a disease associated with abnormal blood cells). Mononuclear blood cells (PBMCs) can be harvested from human peripheral blood via conventional methods, for example, density gradient centrifugation using Ficoll. The PBMCs thus prepared may be cultured in a suitable enriching medium for a suitable period (e.g., 1 to 6 days, 2-4 days, or 3 days) to allow expansion of erythroid progenitor cells (an expansion stage). In some instances, the PBMCs may be washed by a suitable medium for one or more times prior to the culturing. The enriched erythroid progenitor cells can then be subjected to cell sorting to produce a population of early-stage BFU-E cells as described herein.

In other embodiments, the erythroid progenitor cells can be derived from human cord blood, which can be collected from a suitable subject (e.g., a healthy new-born infant or a new-born infant having a disease such as a disease associated with abnormal blood cells). CD34+ cells can be separated from cord blood using a conventional method. CD34 is a cell surface glycoprotein and functions as a cell-cell adhesion factor. Many human progenitor cells express this cell surface marker. Novershtern et al., Cell 144:296-309, 2011. Any type of CD34+ progenitor cells that possess the tendency of differentiating into red blood cells can be used for preparing the early-stage BFU-E cell population. Such progenitor cells are well known in the art. See, e.g., Novershtern et al., Cell 144:296-309, 2011.

Various techniques can be used to separate or isolate the $CD34^+$ cell population from a suitable source such as cord blood. For example, antibodies such as monoclonal antibodies binding to CD34 can be used to enrich or isolate $CD34^+$ cells. The anti-CD34 antibodies can be attached to a solid support (e.g. magnetic beads such as DYNABEADS®) such that cells expressing these surface markers are immobilized, thereby allowing for the separation of $CD34^+$ cells from cells that do not express this surface marker. The separation techniques used should maximize the retention of viable cells to be collected. Such separation techniques can result in sub-populations of cells where up to 10%, usually not more than about 5%, preferably not more than about 1%, of the selected cells do not express CD34. The particular technique employed will depend upon the efficiency of separation, associated cytotoxicity, ease and speed of performance, and necessity for sophisticated equipment and/or technical skill.

Similar techniques can be used to separate or isolate the TGFBRIIIlow population from a suitable source. For example, antibodies such as monoclonal antibodies binding to TGFβRIIIlow can be used to enrich or isolate the TGFBRIIIlow cells. The anti-TGFβRIIIlow antibodies can be attached to a solid support such that cells expressing these surface markers are immobilized, thereby allowing for the separation of TGFBRIIIlow cells from other cells. Exemplary antibodies useful for these methods include, but are not limited to, galunisertib (LY2157299), sc-74511 and (Santa Cruz) and 1C5H11 (ThermoFisher). The separation techniques used should maximize the retention of viable cells to be collected. Such separation techniques can result in sub-populations of cells where up to 10%, usually not more than about 5%, preferably not more than about 1%, of the selected cells are not TGFBRIIIlow cells.

The antibodies used in these methods may be used alone or optionally may be conjugated to a detectable label. Alternatively they may be used with a secondary antibody conjugated to a detectable label. For instance the purification may utilize FACS.

The term "about" or "approximately" means within an acceptable error range for the particular value as determined by one of ordinary skill in the art, which will depend in part on how the value is measured or determined, i.e., the limitations of the measurement system. For example, "about" can mean within an acceptable standard deviation, per the practice in the art. Alternatively, "about" can mean a range of up to ±20%, preferably up to ±10%, more preferably up to ±5%, and more preferably still up to ±1% of a given value. Alternatively, particularly with respect to biological systems or processes, the term can mean within an order of magnitude, preferably within 2-fold, of a value. Where particular values are described in the application and claims, unless otherwise stated, the term "about" is implicit and in this context means within an acceptable error range for the particular value.

The $CD34^+$ cells thus prepared may be cultured in a suitable enriching medium for a suitable period (e.g., 1 to 6 days, 2-4 days, or 3 days) to allow expansion of erythroid progenitor cells (an expansion stage). In some instances, the $CD34^+$ cells may be washed by a suitable medium for one or more times prior to the culturing. Optionally, the expanded erythroid progenitor cells may be further cultured in a suitable preliminary differentiation medium for a suitable period of time, for example, 1-6 days (e.g., 2-4 days or 3 days), to synchronize erythroid progenitors at different development stages to BFU-E cells (a preliminary differentiation stage). The cells can then be harvested and subjected to cell sorting to produce a population of early-stage BFU-E cells as described herein.

Any culture conditions allowing for proliferation of erythroid progenitor cells can be used in the methods described herein. As used herein, expansion or proliferation includes any increase in cell number. Expansion includes, for example, an increase in the number of erythroid progenitor cells over the number of other cells in the cell population used to initiate the culture. Expansion can also include increased survival of existing erythroid progenitor cells. The term survival refers to the ability of a cell to continue to remain alive or function.

A population of cells containing erythroid progenitor cells (e.g., PBMCs or $CD34^+$ cells from cord blood) can be placed in a suitable container for expanding the progenitor cells. For example, suitable containers for culturing the population of cells include flasks, tubes, or plates. In one embodiment, the flask can be T-flask such as a 12.5 $cm^2$, or a 75 $cm^2$ T-flask. The plate can be a 10 cm plate, a 3.5 cm plate, or a multi-welled plate such as a 12, 24, or 96 well plate. The wells can be flat, v-bottom, or u-bottom wells. The containers can be treated with any suitable treatment for tissue culture to promote cell adhesion or to inhibit cell adhesion to the surface of the container. Such containers are commercially available from Falcon, Corning and Costar. As used herein, "expansion container" also is intended to include any chamber or container for expanding cells whether or not free standing or incorporated into an expansion apparatus.

The cell density of the cultured population of erythroid progenitor cells can be at least from about $1\times10^2$ cells to about $1\times10^7$ cells/mL. Preferably, the cell density can be from about $1\times10^5$ to about $1\times10^6$ cells/mL. The cells can be cultured at an oxygen concentration of from about 2 to 20%.

In one example, the expansion stage of any of the methods described herein for preparing the early-stage BFU-E cells can be performed as follows. A population of human PBMCs or $CD34^+$ blood cells, which may be derived from human cord blood, can be placed in an expansion container at a cell density of $10\times10^4$-$10\times10^6$ (e.g., $1\times10^5$) cells/mL. The PBMC or $CD34^+$ cells can be cultured in an expansion medium (e.g., those described herein) supplemented with a mixture of suitable cytokines or growth factors, for example, a steroid such as DEX, SCF, IL-3, and Epo, and penicillin and streptomycin under suitable conditions (e.g., 37° C.) for 1-6 days (e.g., 2-5 days, 3-4 days, or 4 days). The expanded PBMC or CD34+ cells can be collected and subjected to cell sorting for producing the early-stage BFU-E cells.

The base medium for both the expansion medium and the preliminary differentiation medium may be any suitable medium for growth of human cells, particularly stem cells. One example is Iscove's Modified Dulbecco's Media (IMDM). Other examples include, but are not limited to, Dulbecco's MEM, X-Vivo 15 (serum-depleted) and RPMI-1640. Such culture media can be serum free or contain serum. In one embodiment, the medium is serum free STEMSPAN® (Stem Cell Technologies), which can be supplemented with 10 μg/ml heparin. The base medium may be supplemented with fetal bovine serum, detoxified bovine serum albumin (BSA), glutamine, β-mercaptoethanol, β-estradiol, a cytokine, a growth factor, antibiotics (e.g., penicillin and streptomycin) or a combination thereof at suitable concentrations. In other examples, the medium may be serum free.

The expansion medium (and any of the preliminary media and differentiation media) may contain one or more cytokines. As used herein, cytokines are factors that exert a variety of effects on cells, for example, growth or proliferation. Non-limiting examples of the cytokines that may be used in one or more stages of the in vitro culturing process (e.g., in the expansion stage or any of the differentiation stages described below) include interleukin-2 (IL-2), interleukin 3 (IL-3), interleukin 6 (IL-6) including soluble IL-6 receptor, interleukin 12 (IL12), G-CSF, granulocyte-macrophage colony stimulating factor (GM-CSF), interleukin 1 alpha (IL-1 .alpha.), interleukin 11 (IL-11), MIP-1α, leukemia inhibitory factor (LIF), c-kit ligand, and flt3 ligand. In some examples, the in vitro culturing process described herein, or any stages thereof, can include culture conditions, in which one or more cytokine is specifically excluded from the culture medium. Cytokines are commercially available from several vendors such as, for example, Amgen (Thousand Oaks, Calif.), R&D Systems and Immunex (Seattle, Wash.). Cytokine can also include fibroblast growth factor (FGF) (e.g., FGF-1 or FGF-2), insulin-like growth factor (e.g., IGF-2, or IGF-1), thrombopoietin (TPO), and stem cell factor (SCF), or analogs and equivalents thereof. Equivalents thereof include molecules having similar biological activity to these factors (e.g., FGF, TPO, IGF, and SCF) in wild-type or purified form (e.g., recombinantly produced). Analogs include fragments retaining the desired activity and related molecules. For example, TPO is a ligand of the mpl receptor, thus molecules capable of binding the mpl receptor and initiating one or more biological actions associated with TPO binding to mpl are also within the scope of the invention. An example of a TPO mimetic is found in Cwirla et. al. (1997) Science 276:1696. The cytokines for use in the methods described herein, for example SCF, can be a naturally-occurring protein from a suitable source, e.g., human or a non-human mammal. It may also be a genetically engineered version of a wild-type counterpart having similar biological functions.

In some examples, the expansion medium comprises interleukin 3 (IL-3), stem cell factor (SCF), erythropoietin (Epo), and a synthetic steroid such as glucocorticoid (e.g., dexamethasone or DEX) as suitable concentrations. Epo includes naturally-occurring EPOs from a suitable source (e.g., human and a non-human mammal), as well as EPO analogs such as Epoetin alfa, Epoetin beta, or Darbepoetin alfa.

In some examples, the concentration of the synthetic steroid such as DEX may range from 100 nM to 5 μM (e.g., 100 nM to 2 μM, 500 nM to 5 μM, 1 μM to 3 μM, 1 μM to 2 μM, or 2 μM to 5 μM). The concentration of IL-3 may range from 1-10 ng/ml (e.g., 1-8 ng/ml, 1-5 ng/ml, 3-6 ng/ml, 4-8 ng/ml, or 5-10 ng/ml). The concentration of SCF may range from 10-500 ng/ml (e.g., 10-300 ng/ml, 50-500 ng/ml, 50-200 ng/ml, 50-100 ng/ml, 100-200 ng/ml, or 100-400 ng/ml). Alternatively or in addition, the amount of EPO may range from 2-10 U (e.g., 2-8 U, 2-6 U, 5-10 U, or 6-10 U). As well known in the art, one EPO unit elicits the same erythropoiesis stimulating response in rodents (historically: fasted rats) as five micromoles of cobaltous chloride. See, e.g., Jelkmann, Nephrol Dial. Transplant, 2009.

Comparing to the expansion medium, the preliminary differentiation medium may further comprise holo human transferrin and insulin at suitable concentrations. For example, the concentration of holo human transferrin ranges from 250-1,500 μg/ml (e.g., 250-1,000 μg/ml; 300-800 μg/ml, or 400-600 μg/ml); and the concentration of insulin can range from 5-20 μg/ml (e.g., 5-15 μg/ml, 5-10 μg/ml, or 10-20 μg/ml).

The erythroid progenitor cells may be cultured under hypoxic conditions. For example, the hypoxic conditions can comprise 3-15%, e.g., 5-10% $O_2$, 3-10%, e.g., about 5% $CO_2$, and/or balance $N_2$.

The erythroid progenitor cells produced as described herein can be used for isolation of early-stage BFU-E cells. The isolation step may be performed by sorting out the 1-40% erythroid cells expressing the lowest level of TGFβRIII from the progenitor cells. In some examples, the 5-35% erythroid cells expressing the lowest level of TGFβRIII can be isolated as the early-stage BFU-E population. In some examples, the 10-30% erythroid cells expressing the lowest level of TGFβRIII can be isolated as the early-stage BFU-E population. In some examples, the 10-20% erythroid cells expressing the lowest level of TGFβRIII can be isolated as the early-stage BFU-E population. In one example, the 10% erythroid cells expressing the lowest level of TGFβRIII can be isolated as the early-stage BFU-E population.

In some embodiments, other erythroid progenitor cell-specific markers may be considered for isolating the early-stage BFU-E cell population. For example, when PBMCs are used as the source for early-stage BFU-E cell preparation, CD71-high could be used as a marker for further enriching the early-stage BFU-E cells. "CD71 high" or "cells expressing a high level of CD71" refers to cells within the population of the 40-50% cells in an erythroid progenitor population that express the highest level of CD71. In some examples, the overlapping population of the 1-40% (e.g., 5-35%, 10-30%, or 10-20%) cells expressing the lowest TGFβRIII and the 40-50% cells expressing the highest CD71 is harvested as the early-stage BFU-E cell population. In other examples, the overlapping population of the 10-30% cells expressing the lowest TGFβRIII and the 40-50% cells expressing the highest CD71 is harvested as the early-stage BFU-E cell population. In one example, the overlapping population of the 10% cells expressing the lowest TGFβRIII and the 40% cells expressing the highest CD71 is harvested as the early-stage BFU-E cell population.

Alternatively, when CD34+ cells from cord blood are used as the source for early-stage BFU-E cell preparation, CD71-low could be used as a marker for further enriching the early-stage BFU-E cells. "CD71 low" or "cells expressing a low level of CD71" refers to cells within the population of the 40-50% cells in an erythroid progenitor population that express the lowest level of CD71. In some examples, the overlapping population of the 1-40% (e.g., 5-35%, 10-30%, or 10-20%) cells expressing the lowest TGFβRIII and the 40-50% cells expressing the lowest CD71 is harvested as the early-stage BFU-E cell population. In other examples, the overlapping population of the 10-30% cells expressing the lowest TGFβRIII and the 40-50% cells expressing the lowest CD71 is harvested as the early-stage BFU-E cell population. In one example, the overlapping population of the 10% cells expressing the lowest TGFβRIII and the 40% cells expressing the lowest CD71 is harvested as the early-stage BFU-E cell population.

The early-stage BFU-E cells described herein may be used for various purposes, for example, those described herein.

Also within the scope of the present disclosure is a cell culture, comprising any of the early-stage BFU-E cells in a suitable medium, such as those described herein. The early-stage BFU-E cells may be in isolated or purified form as described herein. The medium keeps the BFU-E cells alive and grow in vitro, e.g., any of the expansion media described herein. Further, the medium may facilitate synchronization of erythroid progenitor cells at different stages to the BFU stage, for example, any of the preliminary differentiation media. When needed, the medium also facilitates erythropoietic growth, including enucleation of erythroid progenitor cells, for example, any of the differentiation media described herein.

II. Uses of Early-Stage BFU-E Cells (i) Production of Red Blood Cells

The early-stage BFU-E cells described herein may be used for producing mature red blood cells (RBCs). To produce RBCs, the early-stage BFU-E cells can be prepared by any of the methods described herein.

The early-stage BFU-E cells can then be cultured in a suitable medium, e.g., the expansion medium or the preliminary medium, for a suitable period (e.g., 1-10 days, such as 1-8 days, 2-6 days, or 3-5 days) to enrich erythroid progenitor cells. For example, when the early-stage BFU-E cells are derived from human peripheral blood, an expansion medium may be used to enrich erythroid progenitor cells. When the early-stage BFU-E cells are derived from human cord blood, a preliminary differentiation medium may be used for enriching erythroid progenitor cells.

In one example, the BFU-E cells can be cultured for 8 days prior to differentiation. In some examples, the early-stage BFU-E cells are derived from human peripheral blood and the cells can be cultured in an expansion medium as those described herein for a suitable period such as 1-8 days. In other examples, the early-stage BFU-E cells can be derived from human cord blood and the cells can be cultured in a preliminary differentiation buffer such as those described herein for a suitable period, for example, 1 to 8 days.

Differentiation of the enriched erythroid progenitor cells into RBCs may involve one or more differentiation stages (1, 2, 3, 4, or more), in which the erythroid progenitor cells differentiate into mature enucleated red blood cells. In each differentiation stage, the enriched erythroid progenitor cells prepared by the processes as described herein or cells obtained from the preceding differentiation stage can be cultured in a medium comprising one or more suitable cytokines (e.g., those described herein) under suitable conditions for a suitable period of time. Biological properties of the cells, such as cell size and expression of surface markers, may be monitored during the course or at the end of each differentiation stage to evaluate the status of erythropoiesis. Whenever necessary, cytokines can be timely supplied and/or withdrawn at each differentiation stage to achieve optimal erythroid differentiation and/or synchronizing the cell population in culture.

At each of the differentiation stages, the enriched erythroid progenitor cells, or cells obtained from the preceding differentiation stage can be cultured in a suitable medium (a differentiation medium) under suitable culturing conditions for a suitable period of time, for example 4-12 days (e.g., 5-10 days, 6-8 days, or 7-8 days). The differentiation medium can facilitates erythropoietic growth, including enucleation of erythroid progenitor cells.

The differentiation medium may be any of the base medium described herein supplemented with a suitable mixture of growth factors and/or cytokines, which are known in the art or disclosed herein. In some examples, the differentiation medium may comprise holo human transferrin, SCF and Epo at suitable concentrations, including those described herein. Erythroid progenitor cells derived from human peripheral blood may be differentiated in this medium. In other examples, the differentiation medium may further comprise insulin at a suitable concentration. Erythroid progenitor cells derived from human cord blood may be differentiated in this medium.

The concentrations of the components noted herein can be determined via routine technology and are within the knowledge of a skilled person in the art. For example, the concentration of SCF may range from 10-500 ng/ml (e.g., 10-300 ng/ml, 50-500 ng/ml, 50-200 ng/ml, 50-100 ng/ml, 100-200 ng/ml, or 100-400 ng/ml). Alternatively or in addition, the amount of EPO may range from 2-10 U (e.g., 2-8 U, 2-6 U, 5-10 U, or 6-10 U). Further, the concentration of holo human transferrin ranges from 250-1,500 μg/ml (e.g., 250-1,000 μg/ml; 300-800 μg/ml, or 400-600 μg/m1), and the concentration of insulin can range from 5-20 μg/ml (e.g., 5-15 μg/ml, 5-10 μg/ml, or 10-20 μg/ml).

The differentiation medium may also be supplemented with other components commonly used in cell culture, e.g., fetal bovine serum, glutamine, bovine serum albumin, one or more antibiotics (e.g., penicillin and streptomycin), or any combination thereof.

In some embodiments, differentiation of the erythroid progenitor cells into RBCs may further comprise two additional differentiation stages, Differentiation stage II ("Dif. II"), and Differentiation stage III ("Dif. III").

In Dif. II, the cells obtained from the first differentiation stage as described herein ("Dif I") may be cultured in the presence of a mixture of cytokines including SCF and EPO at suitable concentrations for a suitable period of time (e.g., 3-5 days, 3-4 days, or 4-5 days). In some examples, the concentration of SCF can range from 10-100 ng/ml (e.g., 10-80 ng/ml, 20-80 ng/ml, 20-50 ng/ml, 30-50 ng/ml, 40-50 ng/ml, 50-80 ng/ml, or 50-60 ng/ml). Alternatively or in addition, the amount of EPO can range from 2-10 U (e.g., 2-8 U, 2-6 U, 5-10 U, or 6-10 U). In some examples, the medium used in Dif. II contains holo human transferrin, insulin, SCF, and EPO. This medium may be substantially free of certain cytokines, such as Flt-3, IL-6, dexamethasone, β-estradiol, IL-3, or any combination thereof, or may be substantially free of other cytokines.

In Dif. III, the cells obtained from Dif. II may be cultured in the presence of EPO at a suitable concentration for a suitable period of time (e.g., 4-12 days, 5-10 days, 8-12 days, or 8-10 days). In some examples, the amount of EPO may range from 0.5-3 U (e.g., 1-3 U, 0.5-2 U, 1-2 U, or 2-3 U). In some examples, the medium used in Dif. III contains holo human transferrin, insulin, and EPO. This medium may be substantially free of certain cytokines, for example, Flt-3, IL-6, dexamethasone, β-estradiol, IL-3, SCF, or any combination thereof, or substantially free of other cytokines.

In some embodiments, the in vitro culturing process described herein may include one or any combination of the differentiation stages described herein, for example, Dif. I and Dif. III, Dif. II and Dif. III, or Dif. I and Dif. II.

(ii) Genotoxicity Assay

Figure 5:
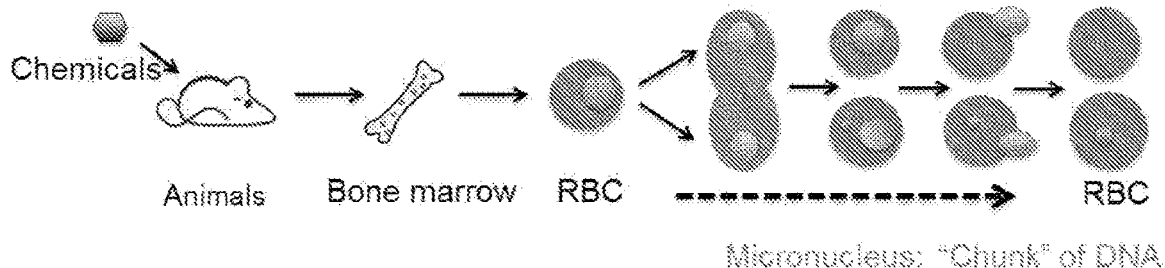
FIG. 5. A diagram showing the conventional animal-based micronucleus test (OECD Test No. 474) for assessing genotoxicity from chemicals.

Micronuclei quantification using erythroblasts from animal bone marrow is a conventional method to assess genotoxicity of leading compounds in the pharmaceutical industry (FIG. 5). In pharmaceutical industry, the animal-based micronucleus test is commonly used to test potential genotoxicity of lead compounds. The compound of interest is injected into mice, and bone marrow cells are extracted to quantify micronuclei. Enucleation is a unique property and is the last step of red cell development. When erythroid progenitor cells exposed to genotoxic chemicals undergo enucleation, there is often a piece of nucleus or a chunk of DNA that is left behind, called the "micronucleus". The frequency of micronuclei is an indicator of the potential of genotoxicity. This in vivo approach would be time-consuming. Also, it cannot be used to screen for compounds having low bioavailability.

Described herein are genotoxicity assays utilizing the early-stage BFU-E cells that can be used to determine whether a candidate compound could induce DNA damage in cells. See, e.g., FIGS. 7-9. To perform the genotoxicity assays, any of the early-stage BFU-E cell population can be first cultured in a suitable medium (e.g., an expansion medium or a preliminary differentiation medium) for a suitable period under sufficient conditions to enrich erythroid progenitor cells as described herein. The enriched progenitor cells can then be subject to differentiation to produce mature RBCs in the presence of a test compound. This differentiation process can be performed by any of the differentiation stages described herein. In some examples, Dif I is performed to produce RBCs from erythroid progenitor cells in the presence of the test compound. Following sufficient exposure to the test compound, the test compound can be washed away, and/or fresh medium (e.g. a differentiation medium) may be added. In some instances, it may not be necessary to wash the cells. In one embodiment, the test compound is added to the culture medium for 4-12 days (e.g., 5-10 days, 6-8 days, or 7-8 days), after which the cells are washed to remove the test compound and fresh culture medium is added.

In one embodiment, the test compound is added to the culture medium at a concentration which is not cytotoxic to the cells. In another embodiment, the test compound is metabolically activated before it is added to the starting population of cells. In one embodiment the test compound is metabolically activated by incubation with liver microsomes or a hepatocyte culture.

The differentiated erythroid cells can be harvested and the level of DNA damage in the harvested cells can be analyzed by a conventional method or a method described herein. An increased level of DNA damage in cells treated with the test compound relative to cells prepared by the same process except for treatment of the test compound indicates that the test compound has potential genotoxicity effects, which can be a clastogenetic effect or an aneugenetic effect.

In some examples, the frequency/percentage of micronuclei (MN) of the differentiated erythroid cells, the number, size and/or shape of polychromatic erythrocytes (PCEs), or a combination thereof, can be measured to determine the level of DNA damage. The percentage of cells comprising micronuclei can be determined by a conventional method, such as flow cytometry, histological analysis and scoring, automated image analysis platforms, or biochemical analyses.

Newly formed erythrocytes, sometimes referred to herein as PCEs, contain ribosomes, mitochondria, and mRNA. Mature erythrocytes are sometimes referred to herein as normochromatic erythrocytes or NCEs. PCEs develop into mature erythrocytes over the three to five days, during which the mRNA is translated and/or degraded. PCEs and mature erythrocytes can be distinguished by staining with Acridine Orange. In addition, the ribosomes and mitochondria in PCEs give them a bluish tint after May-Grunwald staining.

Micronuclei are typically membrane-bound, extra-nuclear, sub-2n DNA structures resulting from double-strand chromosome breaks or from the dysfunction of the mitotic spindle apparatus. Micronuclei, sometimes referred to herein as MN, are also known as Howell-Jolly bodies in the hematology literature.

There are at least four recognized mechanisms by which MNs can develop in poly-chromatic erythrocytes (PCEs): 1) loss of acentric fragments during mitosis, 2) chromosome breakage, 3) loss of entire chromosomes during mitosis, and 4) apoptosis (Heddle, Cimino et al. 1991). Therefore, detection of increased MN-PCE frequency over baseline levels is an indication that the test compound is either a genotoxin or a mitotic spindle poison.

Any method which detects micronuclei can be used in the genotoxicity assay described herein. For example, the percentage of cells comprising micronuclei can be determined by flow cytometry, histological analysis and scoring, and automated image analysis platforms.

The culture can be harvested and analyzed after a period of sufficient length to ensure that an adequate portion of the population has completed terminal erythropoiesis. To harvest cells, the culture can be agitated to detach adherent cells and to create a homogenous suspension. Brief incubation with cell dissociation media (e.g., phosphate buffered saline with 5 mM ethylenediamino tetraacetic acid and 10% FBS) can be used to detach any remaining adherent cells. In certain embodiments, harvested samples can be cytospun onto a microscope slide prior to staining and MN-PCE visualization. Alternatively, cell samples can be fixed and stained in situ before using robotic microscopy and image analysis to quantify MN-PCE frequency. A variety of instrument and software platforms offered by Cellomics, Inc. or other companies are capable of performing this type of automated analysis.

Any visualization technique which allows the detection of MN can be used. In one embodiment, cell samples are air-dried, fixed, and stained with acridine orange (AO) for micronucleus visualization and scoring (Hayashi, Sofimi et al. 1983; Tinwell and Ashby 1989). The application of AO fluorescent staining in the MN test allows the scorer to clearly distinguish DNA from other debris (Hayashi, Sofuni et al. 1983; Tinwell and Ashby 1989). PCEs can be definitively identified using AO staining because they contain single-stranded nucleic acid (RNA) which stains bright orange. NCEs have already translated or degraded all RNA and stain a dull khaki/green color. Finally, AO stains double-stranded nucleic acid (DNA), which is found in nuclei or MN, a bright green.

The population sample can be visualized using fluorescent microscopy and scored to determine the percent of newly-formed RBCs that contain micronuclei. In addition to manual visualization and scoring, many methods are available for high-throughput screening of resulting population. Methods include flow cytometry, laser scanning cytometry, and other technologies that incorporate image analysis software to score the resulting samples (Romagna and Staniforth 1989; Dertinger, Torous et al. 1996; Dertinger, Torous et al. 1997; Styles, Clark et al. 2001). Finally, the slides are scored to determine the frequency of micronucleated polychromatic erythrocytes (MN-PCEs) within the PCE population, which will have been largely formed after exposure to the test compound.

Automated methods of population analysis have been developed to provide two main improvements: 1) higher-throughput analysis, and 2) elimination of scorer-subjectivity from the test (Ashby and Mohammed 1986). Flow cytometric analysis based on erythrocyte markers and DNA stains is one approach used for automated scoring (Dertinger, Torous et al. 1996; Dertinger, Torous et al. 1997).

Another approach employs computerized image analysis to score MN-PCEs on slides by searching for regions with low integral, but high peak, DNA-fluorescence intensity (Romagna and Staniforth 1989; Styles, Clark et al. 2001). Standard laser-scanning cytometry (LSC) focuses on a single plane on the surface of the microscope slide and thus does not provide high-quality images of each individual cell. Another alternative is provided by Cellomics™ image analysis platforms, which provide cell-by-cell focusing and image data for cells that have been stained in multiwell plates. Thus, cells from one million human CD34+ cord blood HSCs can provide erythropoietic cultures in, for example, about 400 to 1000, 96-well plates, and each well can be treated separately. The cells can be fixed and stained in place, in the plates, before being analyzed by robotic microscopy and image analysis.

In some embodiments, the genotoxicity assay described herein can be applied to screen a group of test compounds to determine the genotoxic effect of each individual test compound on erythroid cells. The method comprises selecting at least four individual test compounds to comprise the group of test compounds, and determining the genotoxic effect of each individual test compound on an erythroid cell using the above described method for determining the genotoxic effect of a test compound on an erythroid cell. Any and all embodiments herein described for the method for determining the genotoxic effect of a test compound on an erythroid cell can be applied to the a method for screening a group of test compounds to determine the genotoxic effect of each individual test compound on erythroid cells. In one embodiment the group of test compounds is screened simultaneously in a series of parallel cultures. In one embodiment the group of test compounds comprises at least 30 different individual test compounds. In one embodiment, the group of test compounds comprises at least 300 different individual test compounds. In one embodiment the group of test compounds comprises at least 3000 different individual test compounds.

In other embodiments, each genotoxic effect of an individual test compound is determined in the method for screening a group of test compounds, at multiple concentrations for that compound. In one embodiment the genotoxic effect of an individual test compound is determined for at least 5 different concentrations. In another embodiment the genotoxic effect of an individual test compound is determined for at least 25 different concentrations.

Further, the present disclosure provides a genotoxicity assay which does not require isolation of the early-stage BFU-E cells. To perform this assay, PBMCs can be isolated from peripheral blood obtained from a suitable subject, such as a human subject, via conventional methods and those described herein. The human subject can be a human having an elevated level of erythroid progenitor cells in PBMCs as compared to the representative level of erythroid progenitor cells in a human population, for example, a population of humans having the same gender, age, ethnic background, and/or other similar physical features, such as body weight. Such a human subject may be a healthy subject, or a human patient having a disease, for example, a disease associated with abnormal blood cells as those described herein.

The PBMCs can be cultured in a suitable medium, for example, an expansion medium as described herein, for a suitable period (e.g., 4-12 days) under suitable conditions to expand erythroid progenitor cells in the PBMCs. In some examples, the expansion stage can be 6-10 days, 6-8 days, or 7-8 days. The expanded erythroid progenitor cells can then be cultured in a suitable medium such as a differentiation medium described herein in the presence of a test compound for a suitable period (e.g., 4-12 days) under suitable conditions allowing for differentiation of the erythroid progenitor cells into RBCs, for example, mature RBCs. The differentiated cells can be harvested and the level of DNA damage in the differentiated cells can be examined. A higher DNA damage level of the differentiated erythroid cells as compared with differentiated erythroid cells prepared by the same method except for presence of the test compound indicates that the test compound has potential genotoxicity effects. The level of DNA damage can be measured by any suitable method, such as those known in the art and/or described herein.

The genotoxicity assay described herein can use the culture systems as also described herein, along with automated analysis, to conduct a variety of high-throughput assays, including screening multiple dose-compound combinations for DNA damage effects such as micronucleus induction effects.

(iii) Drug Sensitivity Assessment

Figure 10:
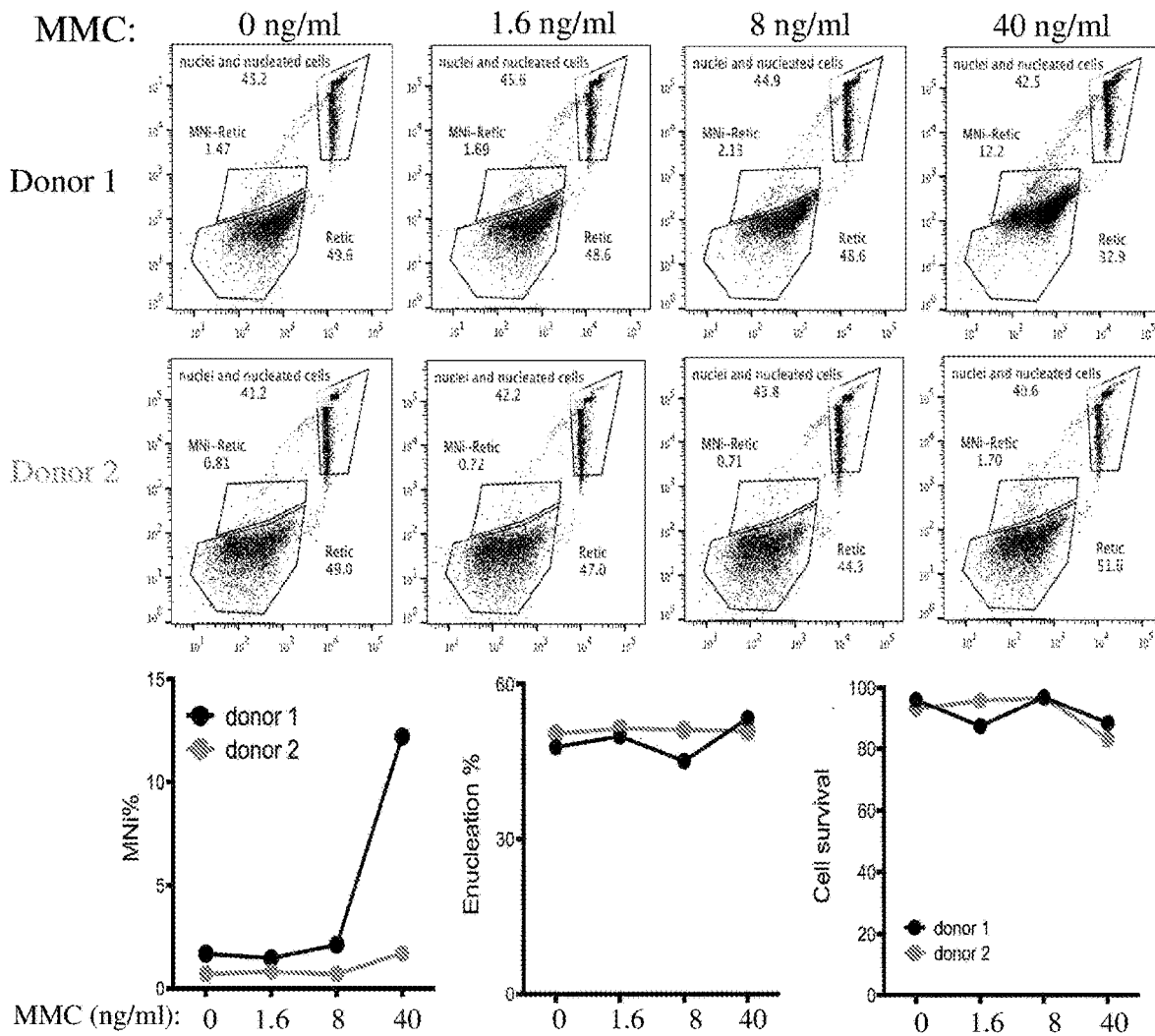
FIG. 10. A diagram showing individual donors having different responses to the same compound.

Any of the genotoxicity assays as described herein can be applied to determine differential drug responses among different individuals. See, for example, FIG. 10. In this case, a candidate therapeutic agent can be analyzed in the genotoxicity assay described herein, using either the early-stage BFU-E cells or PMBCs obtained from an individual as described herein. In some examples, the individual is a human patient having a disease and the therapeutic agent is a candidate for treating that disease. A genotoxicity effect of the therapeutic agent as determined by any of the genotoxicity assays described herein is an indication that the human patient may be sensitive to the therapeutic agent. For example, in the case of a disease in which the therapeutic mechanism of the agent involves causing DNA damage (e.g., a cytotoxic agent for treating cancer), the method may be used to determine whether the agent is likely to be effective in that particular patient (e.g., with a high degree of genotoxicity indicating likely effectiveness). In the case of a disease in which the therapeutic mechanism of the agent does not involve DNA damage and in which genotoxicity would be an undesirable adverse effect of the agent, the genotoxicity assays described herein may be used to determine whether the patient is likely to be unduly sensitive to the agent (e.g., likely to suffer undesirable levels of DNA damage).

(iv) Drug Development

The early-stage BFU-E cells can also be used for screening drug candidates effective in treating a target disease, such as a disease associated with abnormal blood cells (e.g., anemia, polycythemia vera, erythroid leukemias, and myelodysplastic syndromes (MDS)). See, e.g., FIG. 11.

To perform the screening method, any of the early-stage BFU-E cells described herein can be cultured in a suitable medium (e.g., a differentiation medium described herein) in the presence of a drug candidate for a suitable period (e.g., 4-12 days) under suitable conditions allowing for differentiation of the BFU-E cells to erythroid cells. In some embodiments, the BFU-E cells can be cultured for 6-10 days, 6-8 days, or 7-8 days. Afterwards, the total number of erythroid cells in the culture can be measured using a conventional method. An increase of the total erythroid cell number as relative to erythroid cells prepared by the same method except for presence of the drug candidate indicates that the drug candidate may benefit treatment of the target disease.

The screening method described herein can use the culture system as also described herein, along with automated analysis, to conduct a variety of high-throughput assays, including screening multiple dose-compound combinations for effects of enhancing erythroid production.

(v) Treating Blood Cell-Related Diseases

The early-stage BFU-E cells can also be used for treating diseases associated with abnormal blood cells, which include, but are not limited to, anemia, polycythemia vera, erythroid leukemias, and myelodysplastic syndromes (MDS). In some examples, the disease is DBA. In another instance, because these diseases are associated with abnormally increased red blood cells the BFU-Es may be administered in order to reconstitute the subject's erythroid lineage after treatment (e.g., chemotherapy) that wiped out the endogenous erythroid lineage. In the context of the present disclosure insofar as it relates to any of the disease conditions recited herein, the terms "treat", "treatment", and the like mean to relieve or alleviate at least one symptom associated with such condition, or to slow or reverse the progression of such condition. Within the meaning of the present disclosure, the term "treat" also denotes to arrest, delay the onset (i.e., the period prior to clinical manifestation of a disease) and/or reduce the risk of developing or worsening a disease. For example, in connection with cancer the term "treat" may mean eliminate or reduce a patient's tumor burden, or prevent, delay or inhibit metastasis, etc.

The early-stage BFU-E cells can be mixed with a pharmaceutically acceptable carrier to form a pharmaceutical composition, which is also within the scope of the present disclosure. The phrase "pharmaceutically acceptable", as used in connection with compositions of the present disclosure, refers to molecular entities and other ingredients of such compositions that are physiologically tolerable and do not typically produce untoward reactions when administered to a mammal (e.g., a human). Preferably, as used herein, the term "pharmaceutically acceptable" means approved by a regulatory agency of the Federal or a state government or listed in the U.S. Pharmacopeia or other generally recognized pharmacopeia for use in mammals, and more particularly in humans.

Pharmaceutically acceptable carriers, including buffers, are well known in the art, and may comprise phosphate, citrate, and other organic acids; antioxidants including ascorbic acid and methionine; preservatives; low molecular weight polypeptides; proteins, such as serum albumin, gelatin, or immunoglobulins; amino acids; hydrophobic polymers; monosaccharides; disaccharides; and other carbohydrates; metal complexes; and/or non-ionic surfactants. See, e.g. Remington: The Science and Practice of Pharmacy 20th Ed. (2000) Lippincott Williams and Wilkins, Ed. K. E. Hoover.

To perform the methods described herein, an effective amount of the early-stage BFU-E cells as described herein can be administered into a subject in need of the treatment. The subject may be a human patient or a non-human mammal. The BFU-E cells may be autologous to the subject, i.e., the BFU-E cells are obtained from the subject in need of the treatment, and then they or their progeny (e.g., after expansion and/or differentiation ex vivo) administered to the same subject. Administration of autologous cells to a subject may result in reduced rejection of the host cells as compared to administration of non-autologous cells. Alternatively, the BFU-E cells are allogeneic cells, i.e., the cells are obtained from a first subject, and administered to a second subject that is different from the first subject but of the same species. For example, allogeneic BFU-E cells may be derived from a human donor and administered to a human recipient who is different from the donor. In certain embodiments the administered cells may be differentiated progeny of the BFU-E cells, e.g., RBCs.

As used herein, an effective amount refers to the amount of the respective agent (i.e., the early-stage BFU-E cells or a TGFβ inhibitor as disclosed below) that upon administration confers a therapeutic effect on the subject. Determination of whether an amount of the cells or compounds described herein achieved the therapeutic effect would be evident to one of skill in the art. Effective amounts vary, as recognized by those skilled in the art, depending on the particular condition being treated, the severity of the condition, the individual patient parameters including age, physical condition, size, gender and weight, the duration of the treatment, the nature of concurrent therapy (if any), the specific route of administration and like factors within the knowledge and expertise of the health practitioner. In some embodiments, the effective amount alleviates, relieves, ameliorates, improves, reduces the symptoms, or delays the progression of any disease or disorder in the subject.

In some embodiments, the early-stage BFU-E cells are administered to a subject in an amount effective in enhancing erythroid production by least 20%, e.g., 50%, 80%, 100%, 2-fold, 5-fold, 10-fold, 20-fold, 50-fold, 100-fold or more.

In some embodiments, the early-stage BFU-E cells disclosed herein may be administered to a subject who has been treated or is being treated with a therapeutic agent for treating the target disease. The BFU-E cells may be co-administered with the other therapeutic agent. For example, the BFU-E cells may be administered to a human subject simultaneously with a therapeutic agent. Alternatively, the BFU-E cells may be administered to a human subject during the course of a treatment with the therapeutic agent. In some examples, the BFU-E cells and a therapeutic agent can be administered to a human subject at least 4 hours apart, e.g., at least 12 hours apart, at least 1 day apart, at least 3 days apart, at least one week apart, at least two weeks apart, or at least one month apart.

The efficacy of the treatment described herein may be monitored by routine medical practice.

III. TGF β Inhibiting Agent s for Treating Diseases Associated with Abnormal Blood Cells It was discovered in the present study that a clinically tested anticancer drug that selectively blocks the TGFβRI receptor kinase and thus the TGFβ signaling increases erythroblast production from the human early-stage BFU-E cells, indicating that blocking the TGFβ signaling pathway would benefit treatment of diseases associated with abnormal blood cells, such as those described herein. The methods may also be used ex vivo to increase BFU-E numbers and total red cell production.

The transforming growth factor beta (TGFβ) signaling pathway is involved in many cellular processes in both the adult organism and the developing embryo including cell growth, cell differentiation, apoptosis, cellular homeostasis and other cellular functions. TGFβ superfamily ligands bind to a type II receptor, which recruits and phosphorylates a type I receptor. The type I receptor then phosphorylates receptor-regulated SMADs (R-SMADs) which can now bind the coSMAD SMAD4. R-SMAD/coSMAD complexes accumulate in the nucleus where they act as transcription factors and participate in the regulation of target gene expression.

TGFβ inhibitors for use in the treatment methods described herein may be an agent that inhibits the TGFb signaling by at least 30%, e.g., 40%, 50%, 60%, 70% or higher. In some embodiments, the TGFb inhibitor can block the TGFβ RI kinase activity. Exemplary inhibitors include, but are not limited to, DAN/Fc chimera, GW788388, LY364947, Rep Sox, SB 431542, galunisertib (LY2157299), LDN-193189, LY2109761, SB525334, LDN-214117, SB505124, pirfenidone, and GW788388. To treat the target disease, an effective amount of a TGFβ inhibitor can be administered to a subject in need of the treatment, either taken alone or in combination with an additional therapeutic agent. In some instances, the subject is a human patient having, suspected of having, or at risk for the target disease, for example anemia such as DBA.

The TGFβ inhibitor can be administered by any route, including enteral (e.g., oral), parenteral, intravenous, intramuscular, intra-arterial, intracranial, intramedullary, intrathecal, subcutaneous, intraventricular, transdermal, intradermal, interdermal, rectal, intravaginal, intraperitoneal, topical (as by powders, ointments, creams, and/or drops), by any means that facilitate in vivo or ex vivo transport of the compound or composition as described herein in, into, or through tissue/skin of a subject (such as iontophoresis), mucosal, nasal, bucal, sublingual; by intratracheal instillation, bronchial instillation, and/or inhalation; and/or as an oral spray, nasal spray, and/or aerosol. Specifically contemplated routes are oral administration, intravenous administration (e.g., systemic intravenous injection), transfusion, perfusion, regional administration via blood and/or lymph supply, and/or direct administration to an affected site, such as intra-tumoral. In general, the most appropriate route of administration will depend upon a variety of factors including the nature of the agent (e.g., its stability in the environment of the gastrointestinal tract), and/or the condition of the subject (e.g., whether the subject is able to tolerate oral administration).

The exact amount of a TGFβ inhibitor required to achieve an effective amount will vary from subject to subject, depending, for example, on species, age, and general condition of a subject, severity of the side effects or disorder, identity of the particular compound, mode of administration, and the like. An effective amount may be included in a single dose (e.g., single oral dose) or multiple doses (e.g., multiple oral doses). In certain embodiments, when multiple doses are administered to a subject or applied to a biological sample, tissue, or cell, any two doses of the multiple doses include different or substantially the same amounts of a compound described herein. In certain embodiments, when multiple doses are administered to a subject or applied to a biological sample, tissue, or cell, the frequency of administering the multiple doses to the subject or applying the multiple doses to the tissue or cell is three doses a day, two doses a day, one dose a day, one dose every other day, one dose every third day, one dose every week, one dose every two weeks, one dose every three weeks, or one dose every four weeks. In certain embodiments, the frequency of administering the multiple doses to the subject or applying the multiple doses to the tissue or cell is one dose per day. In certain embodiments, the frequency of administering the multiple doses to the subject or applying the multiple doses to the tissue or cell is two doses per day. In certain embodiments, the frequency of administering the multiple doses to the subject or applying the multiple doses to the tissue or cell is three doses per day. In certain embodiments, when multiple doses are administered to a subject or applied to a biological sample, tissue, or cell, the duration between the first dose and last dose of the multiple doses is one day, two days, four days, one week, two weeks, three weeks, one month, two months, three months, four months, six months, nine months, one year, two years, three years, four years, five years, seven years, ten years, fifteen years, twenty years, or the lifetime of the subject, biological sample, tissue, or cell. In certain embodiments, the duration between the first dose and last dose of the multiple doses is three months, six months, or one year. In certain embodiments, the duration between the first dose and last dose of the multiple doses is the lifetime of the subject, biological sample, tissue, or cell. In certain embodiments, a dose (e.g., a single dose, or any dose of multiple doses) described herein includes independently between 0.1 µg and 1 µg, between 0.001 mg and 0.01 mg, between 0.01 mg and 0.1 mg, between 0.1 mg and 1 mg, between 1 mg and 3 mg, between 3 mg and 10 mg, between 10 mg and 30 mg, between 30 mg and 100 mg, between 100 mg and 300 mg, between 300 mg and 1,000 mg, or between 1 g and 10 g, inclusive, of a compound described herein. In certain embodiments, a dose described herein includes independently between 1 mg and 3 mg, inclusive, of a compound described herein. In certain embodiments, a dose described herein includes independently between 3 mg and 10 mg, inclusive, of a compound described herein. In certain embodiments, a dose described herein includes independently between 10 mg and 30 mg, inclusive, of a compound described herein. In certain embodiments, a dose described herein includes independently between 30 mg and 100 mg, inclusive, of an inhibitor described herein.

Dose ranges as described herein provide guidance for the administration of provided pharmaceutical compositions to an adult. The amount to be administered to, for example, a child or an adolescent can be determined by a medical practitioner or person skilled in the art and can be lower, higher, or the same as that administered to an adult.

A TGFβ inhibitor, such as those described herein, can be administered in combination with one or more additional pharmaceutical agents (e.g., therapeutically and/or prophylactically active agents) useful in treating and/or preventing a proliferative disease and/or infectious disease. The inhibitor can be administered in combination with additional pharmaceutical agents that improve their activity (e.g., activity (e.g., potency and/or efficacy) in treating a disease associated with abnormal blood cells in a subject in need thereof, improve bioavailability, improve safety, reduce drug resistance, reduce and/or modify metabolism, inhibit excretion, and/or modify distribution in a subject, biological sample, tissue, or cell. It will also be appreciated that the therapy employed may achieve a desired effect for the same disorder, for different disorders, and/or it may achieve different effects. In certain embodiments, a pharmaceutical composition described herein including a TGFβ inhibitor is administered to a patient in need thereof, to advantageously treat one or more diseases The TGFβ inhibitor may be administered concurrently with, prior to, or subsequent to one or more additional pharmaceutical agents, which may be useful as, e.g., combination therapies in treating and/or preventing a proliferative disease and/or infectious disease.

Pharmaceutical agents include small organic molecules such as drug compounds (e.g., compounds approved for human or veterinary use by the U.S. Food and Drug Administration as provided in the Code of Federal Regulations (CFR)), peptides, proteins, carbohydrates, monosaccharides, oligosaccharides, polysaccharides, nucleoproteins, mucoproteins, lipoproteins, synthetic polypeptides or proteins, small molecules linked to proteins, glycoproteins, steroids, nucleic acids, DNAs, RNAs, nucleotides, nucleosides, oligonucleotides, antisense oligonucleotides, lipids, hormones, vitamins, and cells. In certain embodiments, the additional pharmaceutical agent is a pharmaceutical agent useful in treating a disease associated with abnormal blood cells such as anemia. In some examples, the anemia is DBA. In certain embodiments, the additional pharmaceutical agent is a pharmaceutical agent approved by a regulatory agency (e.g., the US FDA) for treating the target disease. Each additional pharmaceutical agent may be administered at a dose and/or on a time schedule determined for that pharmaceutical agent. The additional pharmaceutical agents may also be administered together with each other and/or with the compound or composition described herein in a single dose or administered separately in different doses. The particular combination to employ in a regimen will take into account compatibility of the compound described herein with the additional pharmaceutical agent(s) and/or the desired therapeutic and/or prophylactic effect to be achieved. In general, it is expected that the additional pharmaceutical agent(s) in combination be utilized at levels that do not exceed the levels at which they are utilized individually. In some embodiments, the levels utilized in combination will be lower than those utilized individually.

Without further elaboration, it is believed that one skilled in the art can, based on the above description, utilize the present invention to its fullest extent. The following specific embodiments are, therefore, to be construed as merely illustrative, and not limitative of the remainder of the disclosure in any way whatsoever. All publications cited herein are incorporated by reference for the purposes or subject matter referenced herein.

EXAMPLES

Single cell transcriptome analysis on BFU-E cells purified from mouse embryos was conducted to understand the mechanism underlying the heterogeneity in the BFU-E cell population. The results showed that there are two distinct subgroups of mouse BFU-E cells: (a) BFU-E cells expressing a high level of the Type III TGFβ receptor (TGFβ RIII) (TGFβ RIII$^{hi}$), and (b) BFU-E cells expressing a low level of TGFβ RIII (TGFβ RIII$^{lo}$). TGFβ RIII was found to be a biomarker to distinguish "early" and "late" BFU-Es. Expression of TGFβ RIII is correlated with GATA1, a gene encoding an erythroid transcription factor induced during the BFU-E to CFU-E transition. The 10% of the BFU-E population expressing the lowest amount of surface TGFβRIII was found to be enriched for early BFU-Es, and was significantly more responsive to glucocorticoid stimulation as compared to the total BFU-E population. Applying the TGFβ RIII$^{10\%\ low}$ purification method to mobilized human bone marrow CD34+ stem/progenitor cells yielded a >3-fold enrichment of BFU-E cells compared to previously reported methods, as assessed by colony formation. Thus, the TGFβ RIII 10% low population represents earlier BFU-Es with maximal capacity for self-renewal. Indeed signaling by the TGFβ receptor kinases RI and RII is increased in late BFU-E cells. A clinically tested anticancer drug that selectively blocks the TGFβ RI receptor I kinase and TGF-β signaling increases erythroblast production from human BFU-E cells, suggesting the use of TGF-β signaling inhibitors for treating DBA.

MATERIALS AND METHODS

Figure 2:
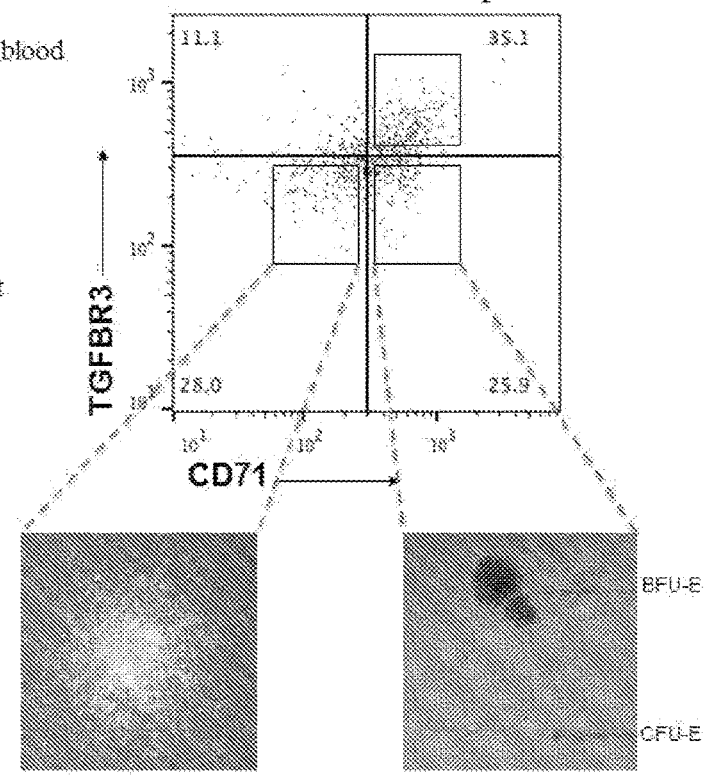
FIG. 2. A diagram showing FACS sorting to isolate human erythroid progenitor derived from human peripheral blood after enrichment phase.
Figure 3:
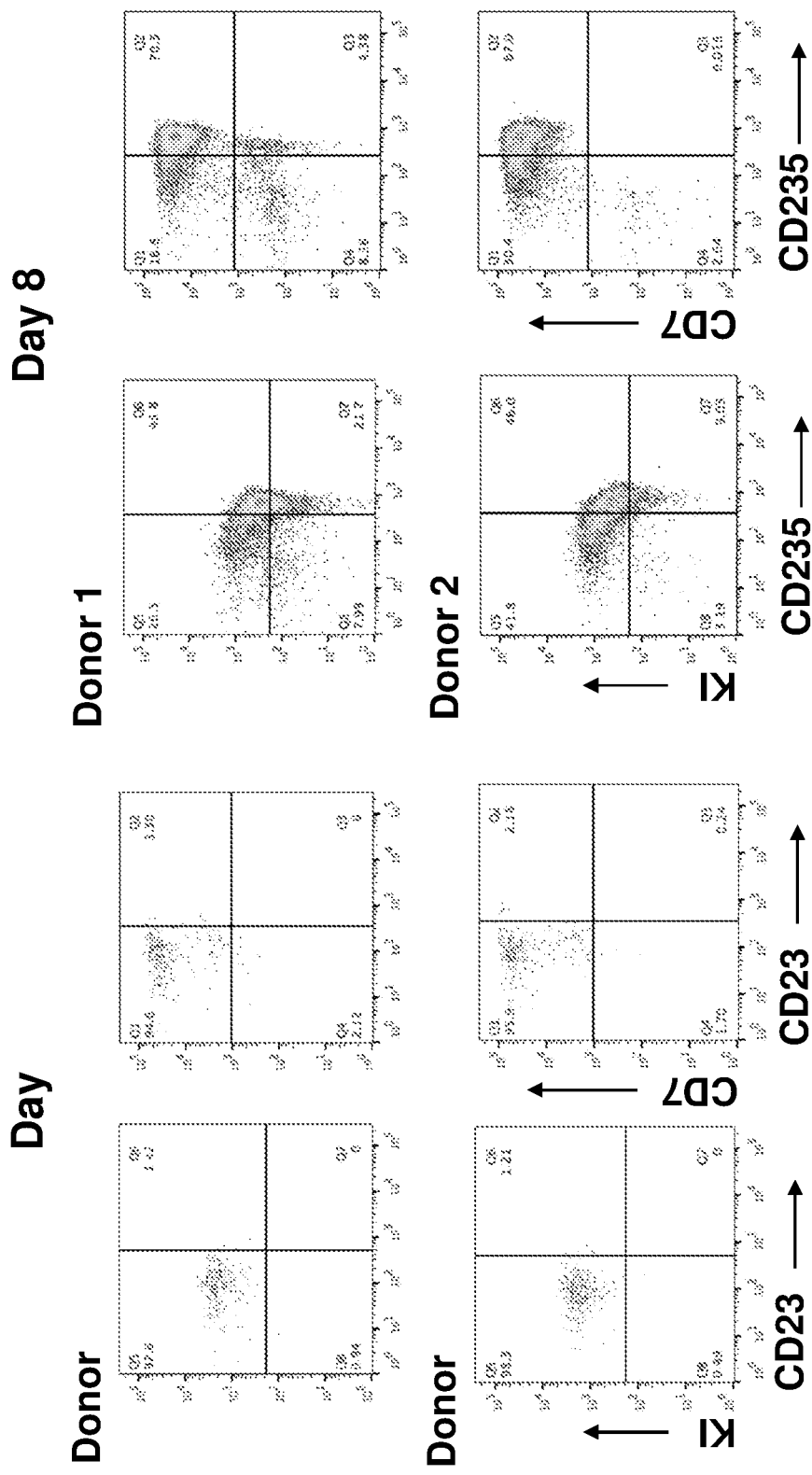
FIG. 3. A diagram showing differentiation of human erythroid progenitors from peripheral or cord blood (TGFβRIII$^{lo}$/CD71$^{hi}$ BFU-E progenitors). Day 4 and Day 8 results.
Figure 4:
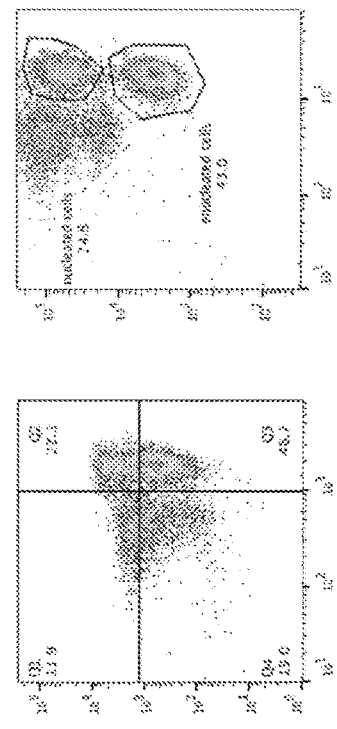
FIG. 4. A diagram showing the differentiation of human erythroid progenitors from human peripheral blood or cord blood (TGFβRIII$^{lo}$/CD71$^{hi}$ BFU-E progenitors). Day 14 and Day 16 results.
Figure 4:
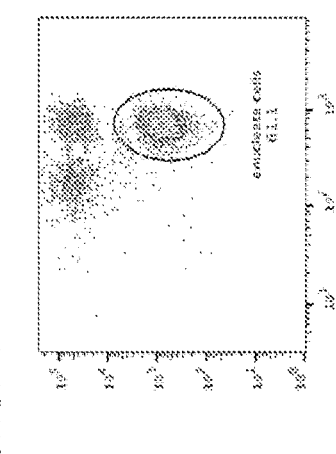
Figure 4:
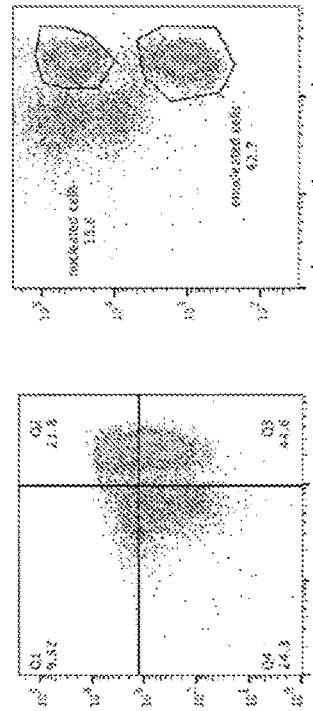

5~10 mL of peripheral blood from healthy human donors or target patients of interest was collected. Mononuclear cells were isolated by FICOLL® (copolymer of sucrose and epichlorohydrin) density gradient centrifugation. The isolated cells were cultured with IMDM medium supplemented with 5 ng/mL IL-3, 100 ng/mL SCF, 2U Epo and 100 nM dexamethasone (DEX) for 3 days (Days 0-3) to enrich for erythroid progenitor cells (FIG. 1, top panel). After enrichment, the CD71 40% high and TGFBR3 10% low erythroid progenitor cells were purified by FACS sorting (FIG. 2). The purified erythroid progenitor cells were expanded in IMDM based medium mentioned above for an additional 8 days (Days 4-12), before switching to erythroid differentiation medium (IMDM, 3% human serum or 5% FBS, 500 µg/mL holo human transferrin, 50 ng/mL SCF, 2U Epo) for 8 days (Days 12~19). During the 8-day differentiation, the surface expression of c-kit gradually decreased, while CD235 level increased (FIG. 3). At Day 19, more than 80% of cells were enucleated to become reticulocytes (FIG. 4).

Figure 6:
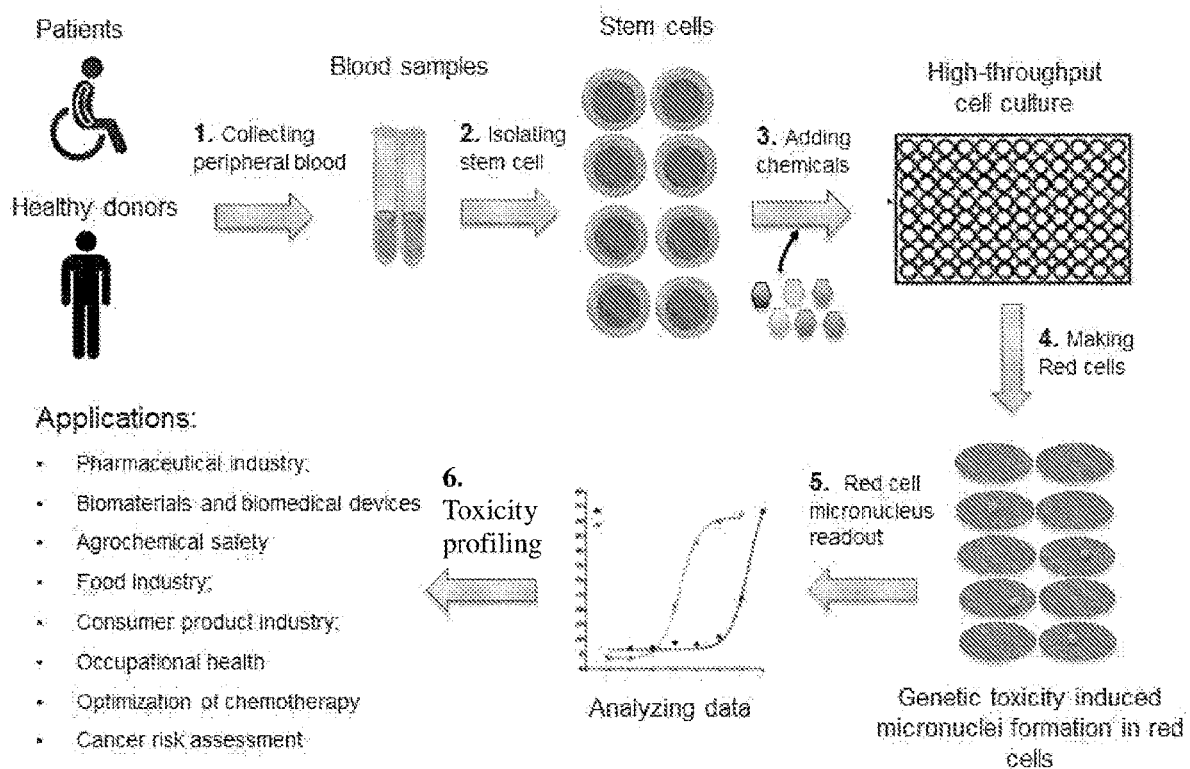
FIG. 6. A diagram showing an exemplary human red cell high throughput platform micronucleus test for assessing genotoxicity. Erythroid progenitors can be isolated from 5~10 mL human peripheral blood from normal donors or patients. These erythroid progenitor cells are then plated in 96-well plates and treated with compounds of interest. The cells are cultured in erythroid differentiation medium, and the frequency of micronuclei is analyzed to assess the genotoxic potential of the compound. This technology can be used in many different industries.

For detecting chemical-induced personal genotoxicity (FIG. 6), the tested chemical was added on Day 12. Erythroid progenitors can be isolated from 5~10 mL human peripheral blood from normal donors or patients. These erythroid progenitor cells were then plated in 96-well plates and treated with compounds of interest. The cells were cultured in erythroid differentiation medium, and the frequency of micronuclei were analyzed to assess the genotoxic potential of the compound (FIG. 6).

Figure 7:
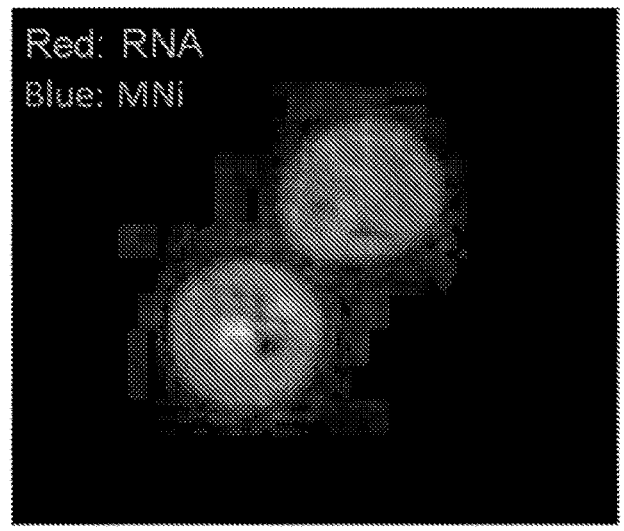
FIG. 7. A photo showing an imaging based method to quantify micronuclei frequency. The cells were stained with DAPI and acridine orange to image micronuclei. DAPI stains for DNA. Acridine orange stains for both DNA and RNA. Acridine orange stains DNA green, and it stains RNA red. Cultured erythroid progenitors were treated with 100 ng/ml mitomycin C for 24 hours. Cells were differentiated into mature human red cells. Cells were fixed in 25° C. methanol for 10 minutes and stained in acridine orange for RNA at a concentration of 20 g/ml and DAPI for DNA in staining buffer.
Figure 8:
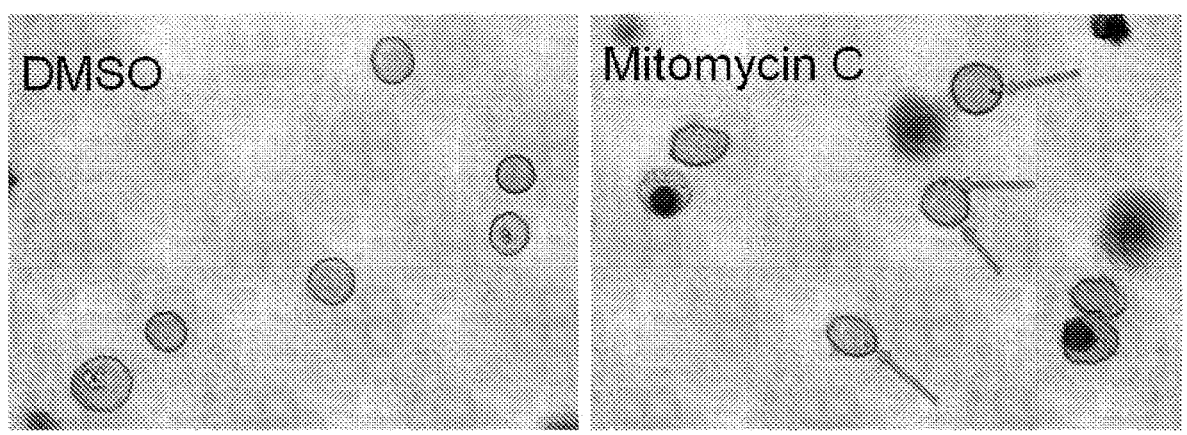
FIG. 8. A photo showing increase of micronuclei when cells were treated with genotoxic chemicals. Bright-field micrograph demonstrated increase of micronuclei after the cells were treated with mitomycin C, a DNA crosslinker and genotoxic agent. Cultured erythroid progenitors were treated with 100 ng/ml mitomycin C or DMSO for 24 hours. Cells were differentiated into mature human red cells. Cells were Giemsa stained and viewed under a microscope.
Figure 9:
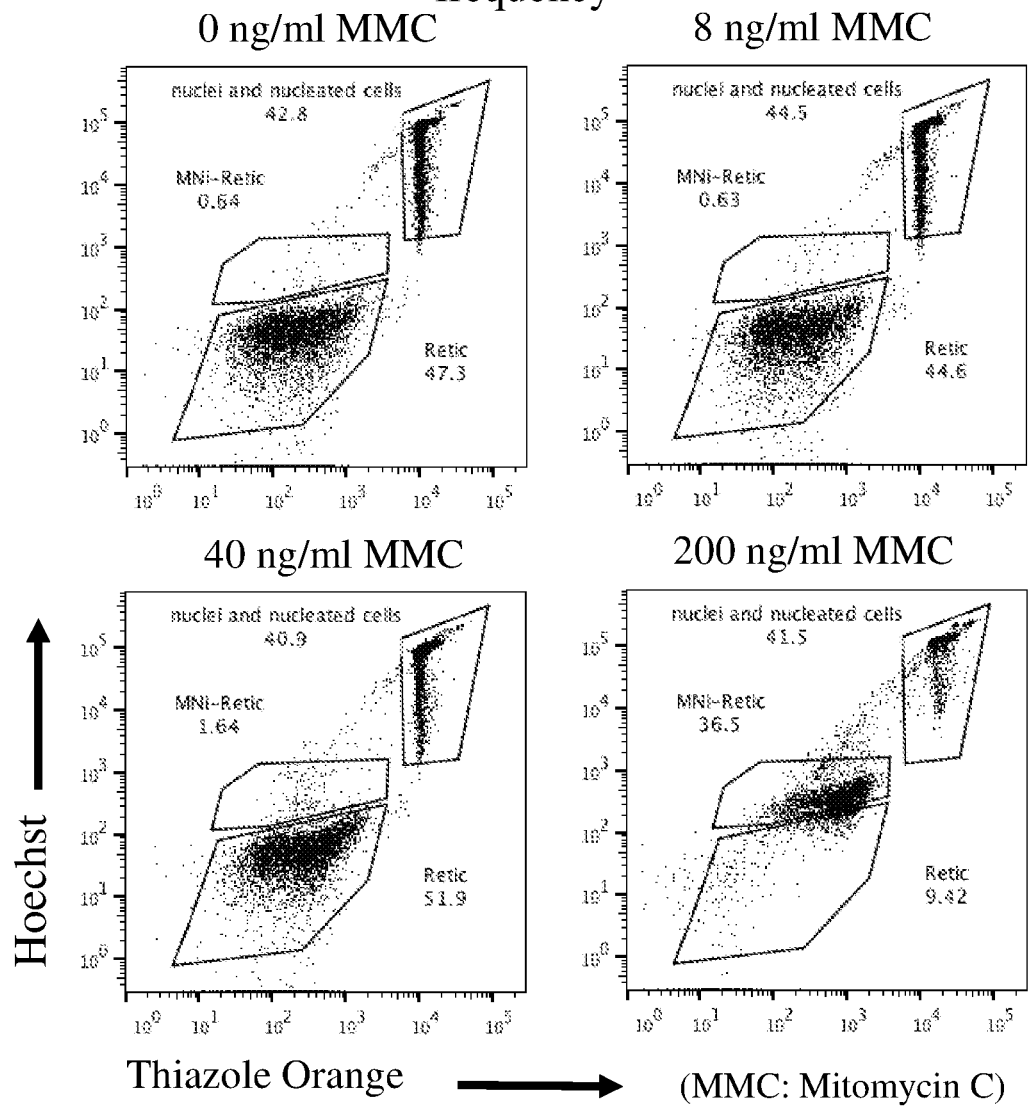
FIG. 9. A diagram showing an exemplary flow cytometry based method to quantify micronuclei frequency. The cells were stained with Hoechst and Thiazole orange to quantify micronuclei. Enucleated reticulocytes (nascent red blood cells) were negative for both Hoechst and Thiazole orange staining, while nucleated cells or nuclei were high for both stains. Cells with micronuclei were higher for both stains compared to reticulocytes. The frequency of micronuclei was dose-dependent on the genotoxic agent.

On Days 16~19, DNA damage level in red blood cells was assessed by quantifying micronuclei frequency. Micronuclei were visible by bright field microscopy (FIG. 8). Micronuclei can be quantified in a high throughput manner by flow cytometry using Hoechst and thiazole orange (FIG. 9), or by an automated imaging system using DAPI and acridine orange staining (FIG. 7).

Figure 11:
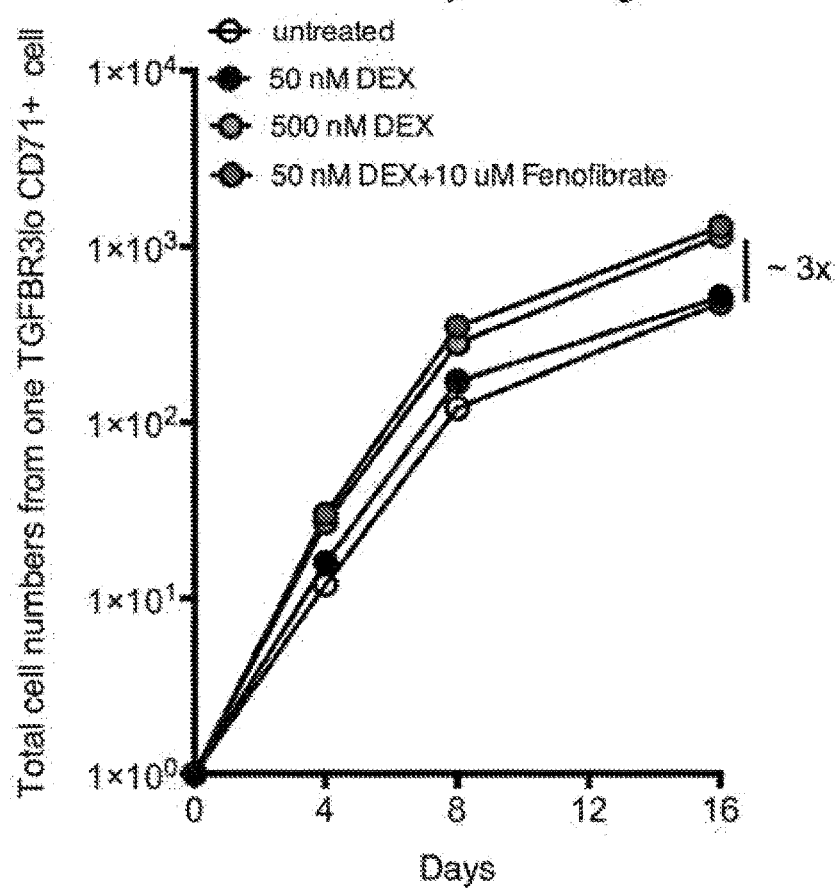
FIG. 11. A chart showing an exemplary application of the human erythroid progenitor culture platform to facilitate discovery of new drugs and identifying new uses of known drugs.
Figure 12:
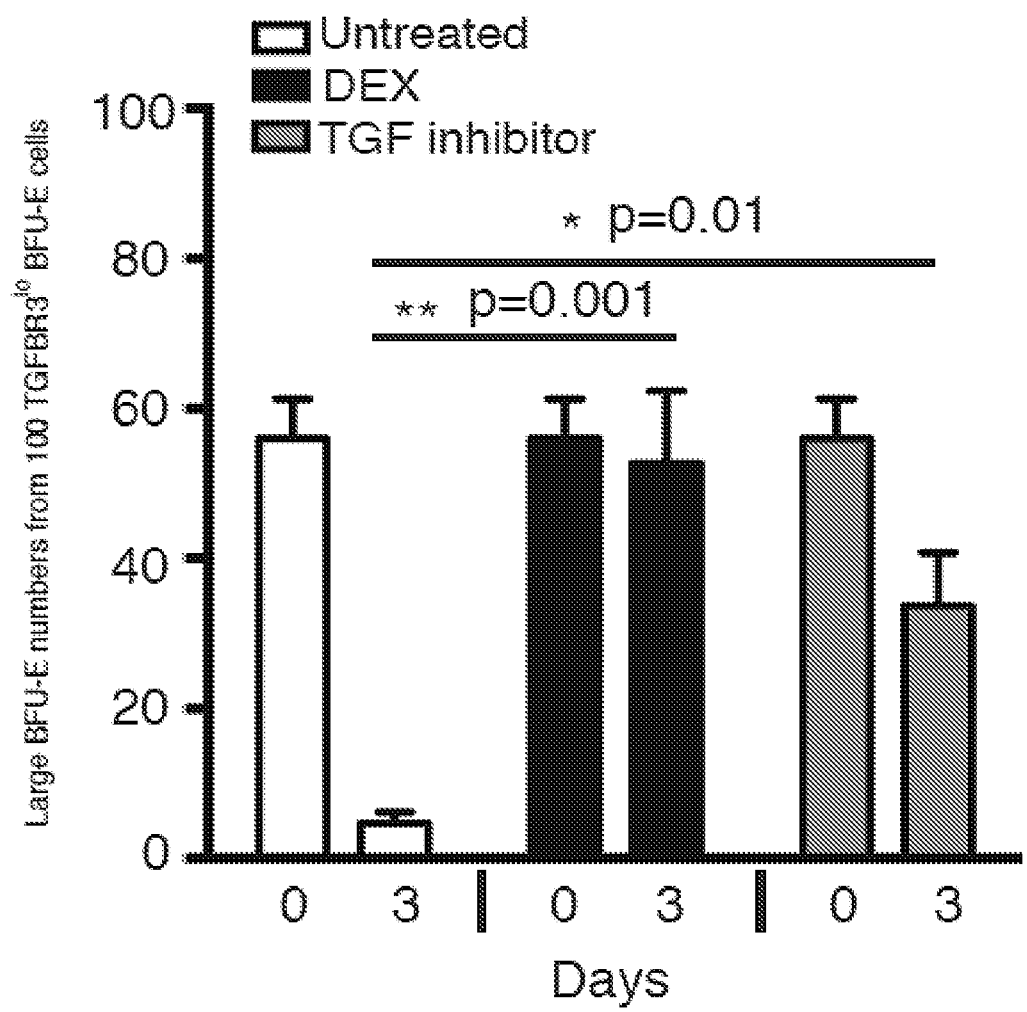
FIG. 12. A chart showing an exemplary colony forming assays were conducted to determine large BFU-E colony numbers from 100 TGFBR3$^{lo}$ mouse BFU-E cells cultured under the indicated conditions. Colony forming assays were performed at indicated time points.
Figure 13:
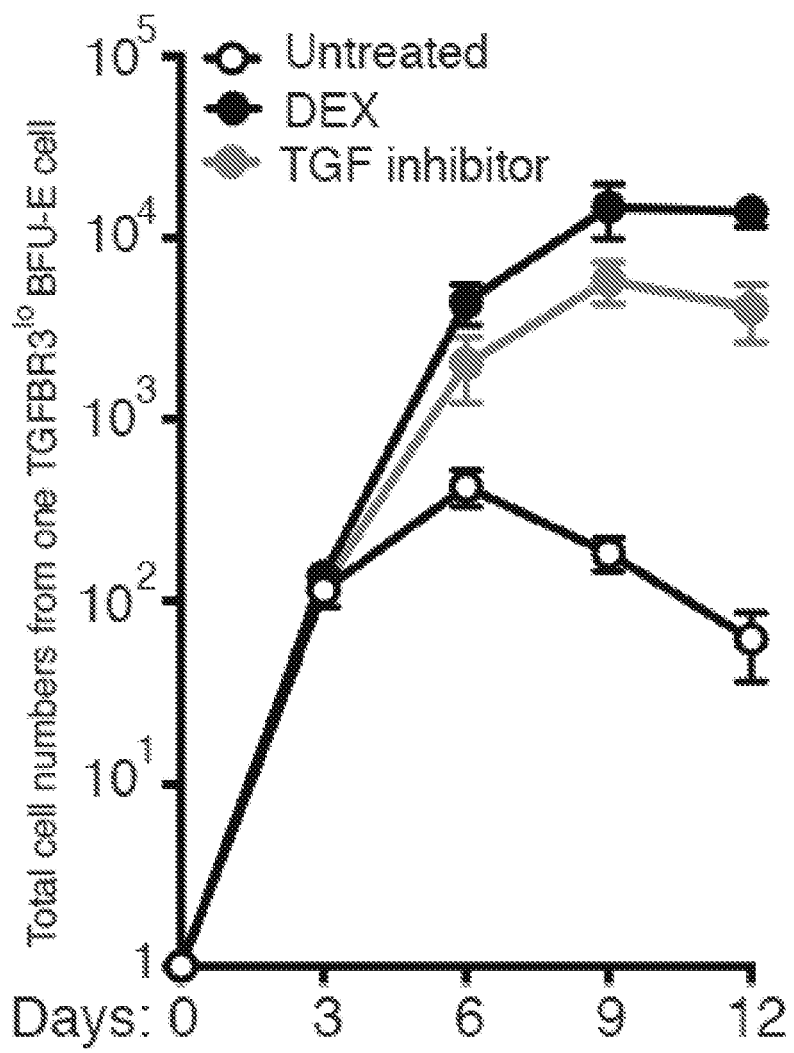
FIG. 13. A chart showing the treatment of purified mouse TGFBR3$^{lo}$ BFU-E cells with DMSO, DEX or TGFβ signaling inhibitor galunisertib. The cells were seeded in SFELE medium supplemented with the test agent.

For new drug discovery or drug repurposing for treating blood diseases, compounds of interest were added into cell culture after progenitor purification. The efficacy of drugs is evaluated based on total red blood cell production, numbers of erythroid progenitor BFU-E and CFU-E (quantified by colony forming assay) and/or level of fetal globin expression. It was shown that DEX synergizes with fenofibrate to increase erythrocyte production from TGFBR3$^{lo}$CD71$^{hi}$ erythroid progenitors (FIG. 11). TGF inhibitor galunisertib (Eli Lilly) was able to increase BFU-E numbers and total red cell production in the culture system (FIGS. 12 and 13).

This erythroid progenitor isolation and culture method can also be applied to cord blood CD34+ cells (FIG. 1, bottom panel). Cord blood CD34$^+$ cells were cultured with IMDM medium supplemented with 5 ng/mL IL-3, 100 ng/mL SCF, 2U Epo and 100 nM dexamethasone for 3 days (Days 0~3) to enrich for erythroid progenitor cells, and then switched to Differentiation I medium for 3 days (Days 4~6) before FACS sorting. The CD71 40% low and TGFBR3 10% low erythroid progenitor cells were purified and continued to be cultured in Differentiation I medium (IMDM supplemented with 5% FBS or 3% human serum, 2 mM glutamine, 500 µg/mL holo human transferrin, 10 µg/mL recombinant human insulin, 100 nM Dexamethasone, 5 ng/mL IL-3, 100 ng/mL SCF and 3U Epo) for 4 days (Days 7~10). On Day 10, cells were switched to Differentiation II medium (IMDM supplemented with 5% FBS or 3% human serum, 2 mM glutamine, 500 µg/mL holo human transferrin, 10 µg/mL recombinant human insulin, 50 ng/mL SCF and 2U Epo) for 8 days (Days 11~18). The cells underwent highly efficient erythroid differentiation similar to erythroid progenitors from peripheral blood.

EQUIVALENTS AND SCOPE

Those skilled in the art will recognize, or be able to ascertain using no more than routine experimentation, many equivalents to the specific embodiments of the invention described herein. The scope of the present invention is not intended to be limited to the above description, but rather is as set forth in the appended claims.

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

What is claimed is:

1. A method for producing red blood cells (RBCs), the method comprising:
    (a) isolating an early-stage burst-forming unit-erythroid (BFU-E) cell population from a starting population of cells, wherein the isolated early-stage BFU-E cell population is composed of no more than the 40% of BFU-E cells in the starting population of cells having the lowest levels of Type III Transforming Growth Factor β Receptor (TGFβRIII);
    (b) culturing the isolated early-stage BFU-E cell population in a first culture medium to provide a population of erythroid progenitor cells; and
    (c) culturing the population of erythroid progenitor cells in a second culture medium to produce red blood cells (RBCs).

2. The method of claim 1, wherein in step (b), the isolated early-stage BFU-E cell population is cultured in the first culture medium for 1 to 10 days.

3. The method of claim 1, wherein the first culture medium comprises interleukin-3 (IL-3), stem cell factor (SCF), erythropoietin (EPO), and a steroid.

4. The method of claim 3, wherein the first culture medium comprises 1 ng/mL to 10 ng/mL IL-3.

5. The method of claim 3, wherein the first culture medium comprises 10 ng/mL to 500 ng/mL SCF.

6. The method of claim 3, wherein the steroid is dexamethasone (DEX), and wherein the first culture medium comprises 100 nM to 5 µM DEX.

7. The method of claim 3, wherein the first culture medium further comprises holo human transferrin and insulin.

8. The method of claim 7, wherein the first culture medium comprises 250 µg/mL to 1,000 µg/mL holo human transferrin.

9. The method of claim 7, wherein the first culture medium comprises 5 µg/mL to 20 µg/mL insulin.

10. The method of claim 3, wherein the first culture medium comprises Iscove's Modified Dulbecco's Media (IMDM).

11. The method of claim 1, wherein the second culture medium comprises holo human transferrin, SCF, and EPO.

12. The method of claim 11, wherein the second culture medium comprises 250 μg/mL to 1,500 μg/mL holo human transferrin.

13. The method of claim 11, wherein the second culture medium comprises 10 ng/mL to 300 ng/mL SCF.

14. The method of claim 11, wherein the second culture medium further comprises insulin and serum.

15. The method of claim 14, wherein the second culture medium comprises 5 μg/mL to 20 μg/mL insulin.

16. The method of claim 11, wherein the second culture medium comprises IMDM.

17. The method of claim 1, wherein in step (c), the erythroid progenitor cells are cultured in the second culture medium for 4 to 12 days.

18. The method of claim 1, wherein the starting population of cells is a population of human peripheral blood cells.

19. The method of claim 1, wherein the starting population of cells is a population of $CD34^+$ progenitor cells.

20. The method of claim 1, wherein the method further comprises, before step (a), providing the starting population of cells.

21. The method of claim 1, wherein the isolating comprises cell sorting.

22. The method of claim 21, wherein the cell sorting comprises fluorescence-activated cell sorting or flow cytometry.

23. The method of claim 1, wherein the isolated early-stage BFU-E cell population is composed of $TGF\beta RIII^{lo}/CD71^{hi}$ erythroid progenitor cells.

24. The method of claim 1, wherein the isolated early-stage BFU-E cell population is composed of $TGF\beta RIII^{lo}/CD71^{lo}$ erythroid progenitor cells.

25. The method of claim 1, wherein the isolated BFU-E cell population is composed of no more than the 35% of BFU-E cells in the starting population of cells having the lowest levels of $TGF\beta RIII$.

26. The method of claim 1, wherein the isolated BFU-E cell population is composed of no more than the 30% of BFU-E cells in the starting population of cells having the lowest levels of $TGF\beta RIII$.

27. The method of claim 1, wherein the isolated BFU-E cell population is composed of no more than the 20% of BFU-E cells in the starting population of cells having the lowest levels of $TGF\beta RIII$.

28. The method of claim 1, wherein the isolated BFU-E cell population is composed of no more than the 10% of BFU-E cells in the starting population of cells having the lowest levels of $TGF\beta RIII$.

\* \* \* \* \*